United States Patent
Taber et al.

(10) Patent No.: US 9,585,656 B2
(45) Date of Patent: Mar. 7, 2017

(54) METHOD AND APPARATUS FOR LOADING AND IMPLANTING A SHAPE MEMORY IMPLANT

(71) Applicant: BioMedical Enterprises, Inc., San Antonio, TX (US)

(72) Inventors: Joseph H. Taber, San Antonio, TX (US); Adam T. Knight, San Antonio, TX (US); Eric A. Marcano, Helotes, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 218 days.

(21) Appl. No.: 14/271,563

(22) Filed: May 7, 2014

(65) Prior Publication Data
US 2014/0358187 A1 Dec. 4, 2014

Related U.S. Application Data

(60) Provisional application No. 61/956,207, filed on Jun. 3, 2013, provisional application No. 61/959,040, filed
(Continued)

(51) Int. Cl.
*A61B 17/06* (2006.01)
*A61B 17/064* (2006.01)
(Continued)

(52) U.S. Cl.
CPC ...... *A61B 17/0642* (2013.01); *A61B 17/0682* (2013.01); *A61B 17/0684* (2013.01); *A61B 17/10* (2013.01); *Y10T 29/49826* (2015.01)

(58) Field of Classification Search
CPC . A61B 17/10; A61B 17/0642; A61B 17/0682; A61B 17/0684
See application file for complete search history.

(56) References Cited

U.S. PATENT DOCUMENTS

| 1,106,241 A | 8/1914 | Richardson |
| 2,544,492 A | 3/1947 | Downing |

(Continued)

FOREIGN PATENT DOCUMENTS

| EP | 0 682 920 A1 | 2/1995 |
| EP | 0 857 462 A1 | 1/1998 |

(Continued)

OTHER PUBLICATIONS

Scott M. Russell, Design Considerations for Nitinol Bone Staples, Journals of Materials Engineering and Performance, vol. 18(5-6), Aug. 2009, USA.

(Continued)

*Primary Examiner* — Andrew Yang
(74) *Attorney, Agent, or Firm* — Christopher L. Makay

(57) ABSTRACT

An implant insertion system includes a shape memory implant movable between a first shape a second shape and an implant insertion device movable between an implant disengagement position and an implant engagement position. The implant insertion device receives the shape memory implant in its first shape while in its implant disengagement position. Movement of the implant insertion device from its implant disengagement position to its implant engagement position manipulates the shape memory implant from its first shape to its second shape. The implant insertion device maintains the shape memory implant in its second shape until delivery of the shape memory implant into tissue or bone.

54 Claims, 42 Drawing Sheets

Related U.S. Application Data on Aug. 13, 2013, provisional application No. 61/959,724, filed on Aug. 30, 2013.

(51) Int. Cl.
A61B 17/068 (2006.01)
A61B 17/10 (2006.01)

(56) References Cited

U.S. PATENT DOCUMENTS

| | | | |
|---|---|---|---|
| 3,939,828 | A | 2/1976 | Mohr et al. |
| 4,438,769 | A | 3/1984 | Pratt et al. |
| 4,485,816 | A | 12/1984 | Krumme |
| 4,665,906 | A | 5/1987 | Jervis |
| 4,869,243 | A | 9/1989 | Huene |
| 5,067,957 | A | 11/1991 | Jervis |
| 5,171,252 | A | 12/1992 | Friedland |
| 5,246,443 | A | 9/1993 | Mai |
| 5,779,707 | A | 7/1998 | Bertholet et al. |
| 5,785,713 | A | 7/1998 | Jobe |
| 6,001,110 | A | 12/1999 | Adams |
| 6,268,589 | B1 | 7/2001 | Flot |
| 6,323,461 | B2 | 11/2001 | Flot |
| 6,412,639 | B1 | 7/2002 | Hickey |
| 6,607,542 | B1 | 8/2003 | Wild |
| 6,685,708 | B2 | 2/2004 | Monassevitch et al. |
| 6,783,531 | B2 | 8/2004 | Allen |
| 7,240,677 | B2 | 7/2007 | Fox |
| 7,344,539 | B2 | 3/2008 | Serhan et al. |
| 7,556,647 | B2 | 7/2009 | Drews et al. |
| 8,118,952 | B2 | 2/2012 | Gall et al. |
| 8,137,351 | B2 | 3/2012 | Prandi |
| 8,191,220 | B2 | 6/2012 | Magnuson et al. |
| 8,211,109 | B2 | 7/2012 | Groiso |
| 8,584,853 | B2 | 11/2013 | Knight et al. |
| 8,596,514 | B2 | 12/2013 | Miller et al. |
| 2005/0043757 | A1 | 2/2005 | Arad et al. |
| 2005/0096660 | A1 | 5/2005 | Allen |
| 2005/0107807 | A1 | 5/2005 | Nakao |
| 2009/0062800 | A1 | 3/2009 | Shano |
| 2009/0272786 | A1 | 11/2009 | Zeiner et al. |
| 2010/0133316 | A1 | 6/2010 | Lizee et al. |
| 2012/0024937 | A1 | 2/2012 | Allen |
| 2012/0085809 | A1* | 4/2012 | Milo ............ A61B 17/0644 227/181.1 |
| 2012/0209305 | A1 | 8/2012 | Deodhar et al. |
| 2013/0026206 | A1 | 1/2013 | Fox |
| 2013/0026207 | A1 | 1/2013 | Fox |
| 2013/0030437 | A1 | 1/2013 | Fox |
| 2013/0030438 | A1 | 1/2013 | Fox |
| 2013/0231667 | A1 | 9/2013 | Taylor et al. |
| 2014/0018809 | A1 | 1/2014 | Allen |
| 2014/0097228 | A1 | 4/2014 | Taylor et al. |
| 2014/0277516 | A1 | 9/2014 | Miller et al. |

FOREIGN PATENT DOCUMENTS

| | | |
|---|---|---|
| EP | 0 826 340 A3 | 3/1998 |
| EP | 0826340 A2 | 3/1998 |
| EP | 1 870 042 | 12/2007 |
| FR | 2874166 A1 | 2/2006 |
| WO | WO 2008/129061 A1 | 10/2008 |
| WO | 2010004330 A1 | 1/2010 |
| WO | WO 2013/055824 A1 | 4/2013 |

OTHER PUBLICATIONS

4-Fusion Shape Memory Implant Training and Demonstration Video and Captured Slide Images, Memometal, Inc., 2008.
4-Fusion Shape Memory Implant Brochure, Memometal, Inc., Jun. 23, 2009.
BioMedical Enterprises, Inc. (BME) v. Solana Surgical, LLC., BME's Disclosure of Initial Infringement Contentions, Jun. 9, 2014.
BioMedical Enterprises, Inc. (BME) v. Solana Surgical, LLC., BME's Opening Claim Construction Brief, Aug. 29, 2014.
BioMedical Enterprises, Inc. (BME) v. Solana Surgical, LLC., Defendant Solana Surgical, LLCs Opening Claim Construction Brief, Aug. 29, 2014.
BioMedical Enterprises, Inc. (BME) v. Solana Surgical, LLC., BME's Responsive Claim Construction Brief, Sep. 19, 2014.
BioMedical Enterprises, Inc. (BME) v. Solana Surgical, LLC., Defendant Solana Surgical, LLCs Responsive Claim Construction Brief, Sep. 19, 2014.
BioMedical Enterprises, Inc. (BME) v. Solana Surgical, LLC., Defendant Solana Surgical, LLCs Initial Invalidity Contentions, Jul. 17, 2014.
BioMedical Enterprises, Inc. (BME) v. Solana Surgical, LLC., Memorandum Opinion and Order Regarding Claim Construction, Nov. 4, 2014.
Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).
Superelastic Fixation System Brochure, Memometal Inc., USA, Aug. 12, 2009.
Shape Memory Staple System for Arthrodesis and Skeletal Fixation of the Hand Brochure, Core Essence Orhtopaedics, Inc., 2009.
E. A. Van Amerongen et al., "Four-Corner Arthrodesis Using the Quad Memory Staple," Journal of Hand Surgery (European vol. 2008) (Jan. 7, 2009).
U. Rethnam et al., "Mechanical Characteristics of Three Staples Commonly Used in Foot Surgery," Journal of Foot and Ankle Research (Feb. 25, 2009) available at http://www.footankleres.com/content/2/1/5.
T. F. Smith, "The Bone Staple: Tried and True Superhero of Bone Fixation," Educational Materials Update Chapter 41 (2010) available at www.podiatryinstitute.com/pdfs/Update 2010/2010 41.pdf.
Elevest Procedure Kit, Instructions for Use by CooperSurgical (©2007).
Agee WristJack, Surgeon's Manual by Hand BioMechanics Labs, Inc. (©1990-2002).
ENTact™ Septal Stapler, Product brochure by ENTrigue Surgical, Inc. (©2009).
R. M. Sloan et al., "Orthopedic Fixation Devices," Radiographics at 823 (Sep. 1991).
J. Arthur, "Improving Operating Efficiency in Five Days," Lean Six Sigma for Hospitals, McGraw-Hill (2011).
K. Yamauchi et al. (ed.), "Shape Memory and Superelastic Alloys: Applications and Technologies" (2011).
BioResearch Innovations (BRI), "Memodyn Compression Staple," FDA 510(K) disclosure (Jan. 2004).
G. C. Taylor et al., "Complications of Internal Fixation," Podiatry Institute Educational Materials Update Chapter 79 (1992).
Wright Medical Technology, Inc., "Charlotte Compression Staple as described by Robert Anderson, MD; Bruce Cohen, MD; and W. Hodges Davis, MD" (2007).
A. A. Weinbroum et al., "Efficiency of the Operating Room Suite," American Journal of Surgery 244-250 (2003).
G. G. Porto, "Safety by Design: Ten Lessons From Human Factors Research," Journal of Healthcare Risk Management 43-50 (Fall 2011).
International Search Report and Written Opinion of the International Searching Authority, International Application No. PCT/US2014/039905 Based on U.S. Appl. No. 14/271,563, BioMedical Enterprises, Inc., May 29, 2014.
Petition for Inter Partes Review (IPR No. 2015-00786), Wright Medical Technology, Inc., Petitioner, v. BioMedical Enterprises, Inc., Patent Owner, U.S. Pat. No. 8,584,853 to Knight et al., Filed Feb. 20, 2015.
Declaration of Dr. Stephen H. Smith, in Support of Petition for Inter Partes Review (IPR No. 2015-00786), Wright Medical Technology, Inc., Petitioner, v. BioMedical Enterprises, Inc. Patent Owner, U.S. Pat. No. 8,584,853 to Knight et al., Filed Feb. 20, 2015.
International Search Report and Written Opinion for PCT/US2014/039905, Oct. 22, 2014.

(56) References Cited

OTHER PUBLICATIONS

MemoGraph Brochure, M.B.A. (Memory Biological Application), Parc Club de Nancy de Brabois, Batiment B11, 4 allee Vincennes, 54500 Vandceurve, France, 1999.
OSStaple Brochure Including pictures of staple loaded in shipping block, BioMedical Enterprises, Inc., 14875 Omicron Drive, Suite 205, San Antonio, TX 78245, 2010.

* cited by examiner

METHOD AND APPARATUS FOR LOADING AND IMPLANTING A SHAPE MEMORY IMPLANT

BACKGROUND OF THE INVENTION

1. Field of the Invention

The present invention relates generally to an implantation device and, more particularly, but not way of limitation, to an implantation device designed for loading with a surgical implant and for subsequent delivery of the surgical implant. The implantation device uses jaws and a spacer to secure a surgical implant and allow implantation into a patient.

2. Description of the Related Art

Shape memory implants are commonly used in surgical procedures that require the reattachment or fusing of tissue or bone. Shape memory implants can be composed of shape memory material such as Nitinol that allows the shape memory implants to have a first final shape and the ability to transform into a second shape. The shape memory material gives the implants elastic properties in that they store mechanical energy and are subject to elastic (recoverable) deformation when they release the stored mechanical energy. The implants are mechanically deformed into their second shape and held in their second shape by instrumentation such that, upon release from the instrumentation, the implants elastically deform from their second shape into their first final shape.

In surgical procedures, the elastic property of shape memory implants is used as follows. Bones that require fixating are aligned, and the shape memory implant, which has been mechanically deformed to its second shape, is held in instrumentation and inserted between the bones. After insertion, the shape memory implant is released from the instrumentation, whereupon the shape memory implant elastically deforms to its first final shape such that the shape memory implant maintains the bones fixated together. Because the shape memory implants stores mechanical energy, it continuously applies force to the fixated bones as the shape memory implant transitions from the second shape to the first final shape, which aids in the healing process.

Shape memory implants require instrumentation to maintain them in their second shape and for insertion into tissue or bone. To facilitate a more efficient surgical procedure, it is beneficial to preload the shape memory implants onto the instrumentation prior to surgery. Preloading shape memory implants onto instrumentation has typically been a two-stage process. In the first stage, the shape memory implant loads onto a constraining device that allows the shape memory implant to be transported and shipped. In the second stage, the shape memory implant is transferred from the constraining device onto instrumentation, and the instrumentation allows the surgeon to implant the shape memory implant into a patient during a surgical procedure.

Transferring the shape memory implant from the constraining device to the instrumentation increases the risk that the shape memory implant may accidently detach from either the constraining device or the instrumentation during a surgical procedure. Often if the shape memory implant detaches, the shape memory implant must be discarded for sanitary or other reasons.

The instrumentation for maintaining the shape memory implants in their second shape is typically forceps or implant insertion devices designed to receive the implants in their second shape. Although potentially effective, forceps require the implant to be loaded into the forceps during surgery, which can be cumbersome and time consuming. In addition, forceps are large which hinders implantation of the shape memory implant into a patient during surgery. Furthermore, forceps can be expensive instruments that require cleaning and sterilization after each surgery.

Implant insertion devices other than forceps tend to be formed around the exact profile of the shape memory implant. This is accomplished by having the implant fit inside a passage that is substantially the same diameter as the shape memory implant. By using this method, the implant insertion device allows the shape memory implant to be preloaded prior to surgery. However, using an implant insertion device that substantially conforms to the profile of the shape memory implant can create several problems for a surgeon. First, this type of implant insertion device often makes removal of the shape memory staple after implantation problematic. In particular, the shape memory implant sticks to the implant insertion device due to the frictional engagement between the shape memory implant, which is trying to compress, and the passage of the implant insertion device, resulting in a more difficult surgical procedure and the potential for a less than satisfactory fixation of tissue or bone. Second, this type of implant insertion device results in an abrupt and sudden release of stored mechanical energy as the implant is removed from the device. This type of implant insertion device provides no method by which to slowly transition the stored energy in the implant from the implant insertion device to the bones that are being fixated. Finally, this type of implant insertion device can result in entanglement during release, in which the implant legs begin to compress upon release and make extraction of this type of insertion device more difficult.

Accordingly, an instrument that constrains a shape memory implant in its second shape, allows the shape memory implant to be preloaded prior to surgery, simplifies removal of the shape memory implant after partial implantation, and controls the rate of release of tension would be beneficial.

SUMMARY OF THE INVENTION

In accordance with a method and apparatus for loading and implanting a shape memory implant, an implant insertion device receives a shape memory implant in a first shape, manipulates the shape memory implant from its first shape to a second shape, and maintains the shape memory implant in its second shape until the delivery of the shape memory implant into tissue or bone. The implant insertion device loaded with the shape memory implant in its second shape may be packaged and sterilized before shipping and use. During surgery, the implant insertion device permits the controlled release of the shape memory implant at the discretion of the surgeon.

The implant insertion device includes a body having a first arm and a second arm and a spacer coupled with the body and movable between an unlocked position and a locked position. In addition, it is evident that there is any number of intermediary positions for the spacer between the unlocked and locked position. The first arm includes a first jaw adapted to engage the shape memory implant. Likewise, the second arm includes a second jaw adapted to engage the shape memory implant. The first jaw and the second jaw are movable from a disengaged position to an engaged position. The spacer in its locked position inserts between one of the first jaw and the second jaw, the first arm and the second arm, and both the first arm and jaw and second arm and jaw. Insertion of the spacer urges the first and second jaws to their engaged positions such that the first and second jaws engage the shape memory implant and move the shape memory implant from its first shape to its second shape. The first and second jaws in their engaged positions maintain the shape memory implant in the second shape until the implant insertion device delivers the shape memory implant into tissue or bone. The first and second arms maintain the first and second jaws canted downward when the spacer resides in its unlocked position. In other words, the first and second arms maintain the first and second jaws such that they are rotated at an angle relative to the arms when the spacer resides in its unlocked position. Consequently, insertion of the spacer between the first and second jaws to its locked position moves the first and second jaws horizontally outward and in an upward arc, as well as also rotating the jaws, to their engaged positions such that the first and second jaws engage the shape memory implant and move the shape memory implant from its first shape to its second shape. The first arm may be shorter in length than the second arm such that the implant insertion device receives a shape memory implant with a first bridge at a height different from a second bridge.

Once the implant insertion device delivers the shape memory implant into tissue or bone, movement of the spacer from its locked position to its unlocked position releases the spacer from between the first jaw and the second jaw. It is noted that the movement of the spacer from its locked position to its unlocked position can be partial, thus partially releasing the spacer and therefore partially and controllably releasing the stored energy of the shape memory implant. The first and second jaws accordingly move from their engaged positions to their disengaged positions such that the first and second jaws disengage from the shape memory implant. Disengagement of the first and second jaws from the shape memory implant releases the shape memory implant and allows the shape memory implant to move from its second shape to its first shape. Because the jaws rotate relative to the arms during disengagement, the jaws thus avoid entanglement with the shape memory implant during release. The user of the implant insertion device can control the rate of release of the shape memory implant and therefore the application of compression force by controlling the rate at which the spacer is moved.

The first jaw includes a leg interface that abuts a first leg of the shape memory implant when the first jaw resides in its engaged position. Similarly, the second jaw includes a leg interface that abuts a second leg of the shape memory implant when the second jaw resides in its engaged position. The first and second jaws each further include an optional bridge interface. When the first and second jaws reside in their engaged positions, at least a portion of the bridge of the shape memory implant can reside atop the bridge interfaces. The first and second jaws also may include a stop disposed above their bridge interfaces. The stops and the bridge interfaces can each define a slot such that, when the first and second jaw resides in their engaged positions, at least a portion of a bridge of the shape memory implant may reside in the slots to allow more stability in retaining the shape memory implant.

The spacer pivotably connects with the body and includes a separator and an actuator adapted to allow movement of the spacer between its unlocked and locked positions. The separator inserts between the first and second jaws and abuts separator interfaces of the first and second jaws to urge the first and second jaws to their engaged positions. The separator defines a space that allows the separator to insert between the first and second jaws without contacting the shape memory implant.

In a method of securing a first bone with a second bone, an implant insertion device loaded with a shape memory implant in the second shape is provided. One of ordinary skill in the art will also note that the first bone could be a bone, bone fragment, tissue, or body structure and the second bone could be a bone, bone fragment, tissue, or body structure and these additional terms are therefore not repeated to avoid confusion. The first bone is positioned relative to the second bone and the shape memory implant is positioned at the first bone and the second bone using the implant insertion device. The shape memory implant is inserted into the first bone and the second bone using the implant insertion device. The spacer is moved at the desired rate from between the first jaw and the second jaw thereby releasing the shape memory implant from the first and second jaws in a controlled fashion, and the implant insertion device is removed from the shape memory implant. As a result, the shape memory implant moves from its second shape to its first shape at a controlled rate, thereby securing the first bone with the second bone. If necessary, the shape memory implant may be tamped into the first bone and the second bone after removing the implant insertion device from the shape memory implant.

The implant insertion device is loaded with a shape memory implant as follows. The first and second jaws of the implant insertion device are contacted with the shape memory implant in its first shape. The shape memory implant is reduced to a temperature at or below a deformation temperature of the shape memory implant. The spacer of the implant insertion device inserts between the first and second jaws at a controlled rate, thereby urging the first and second jaws to engage the shape memory implant and move the shape memory implant from its first shape to its second shape at a controlled rate. The first and second jaws maintain the shape memory implant in the second shape until the delivery of the shape memory implant into tissue or bone. If desired, the implant insertion device loaded with the shape memory implant in its second shape may be packaged and sterilized.

The insertion of the spacer between the first and second jaws may be accomplished as follows. The implant insertion device having its first and second jaws contacted with the shape memory implant in its first shape is placed in a press tool. The press tool is activated at a desired speed to press the implant insertion device and the shape memory implant such that the spacer of the implant insertion device inserts between the first and second jaws and urges the first and second jaws to engage the shape memory implant. As a result, the first and second jaws move the implant from its first shape to its second shape at the rate defined by the press tool. The implant insertion device loaded with the shape memory implant in its second shape is removed from the press tool. The first and second jaws maintain the shape memory implant in the second shape until the delivery of the shape memory implant into tissue or bone.

In a method of loading a plurality of implant insertion devices with a shape memory implant, the plurality of implant insertion devices are movable between an implant disengagement position and an implant engagement position. Each shape memory implant in its first shape is contacted with one of the implant insertion devices in its implant disengagement position. Each shape memory implant contacted with one of the implant insertion devices is reduced via a cryo-freezer to a temperature at or below a deformation temperature of the shape memory implants. After removal from the cryo-freezer, each shape memory implant contacted with one of the implant insertion devices is maintained via a cold table at or below the deformation temperature of the shape memory implants. One of the shape memory implants contacted with an implant insertion device is placed in a press tool. The press tool is activated to press the implant insertion device and the shape memory implant to move the implant insertion device from its implant disengagement position to its implant engagement position. As a result, the implant insertion device moves the shape memory implant from its first shape to its second shape and further maintains the shape memory implant in the second shape. The implant insertion device loaded with the shape memory implant in its second shape is removed from the press tool. The press tool is sequentially used to load each implant insertion device with a shape memory implant in its second shape.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

Figure 1:
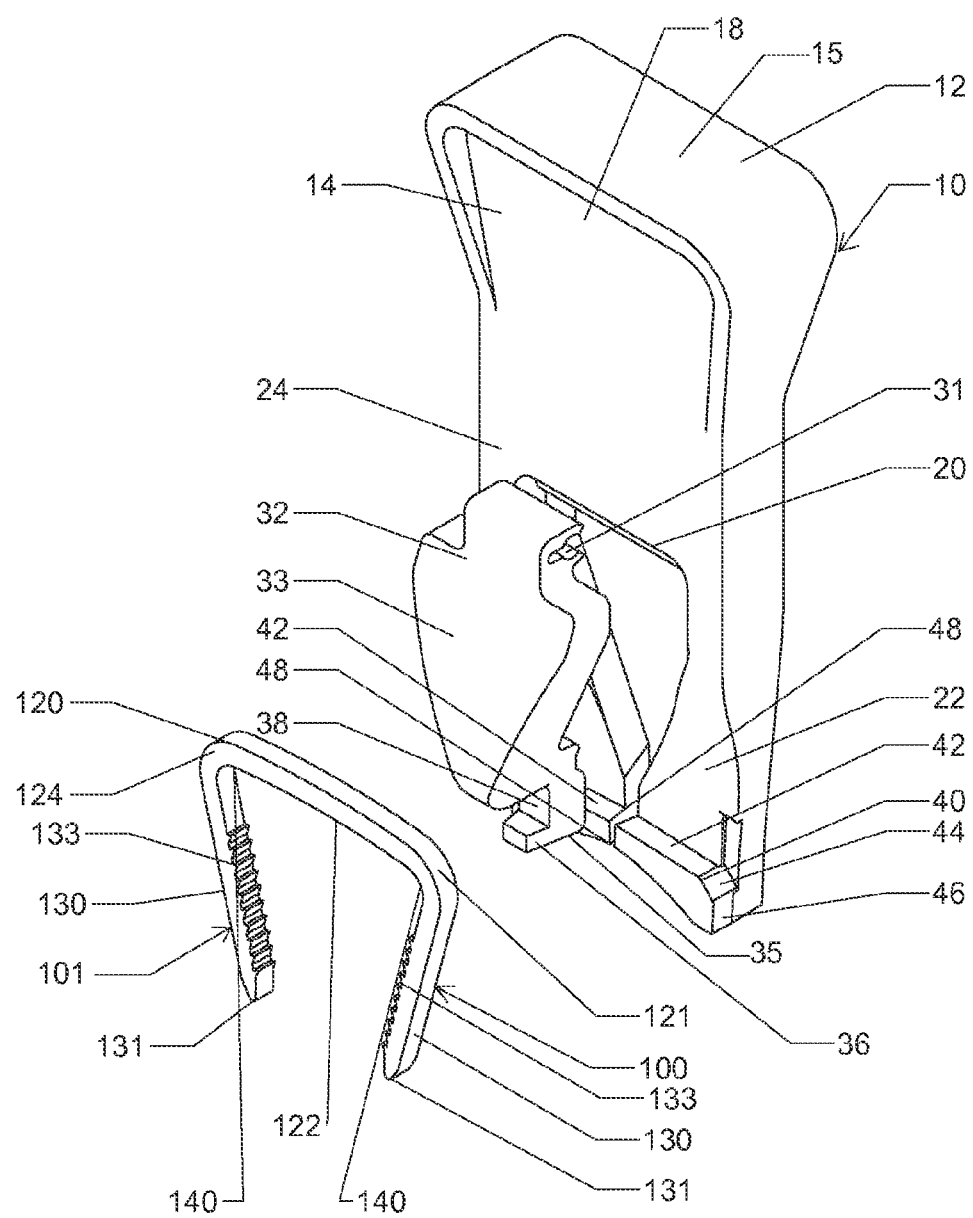
FIG. 1 is an exploded perspective front view illustrating a body and spacer of an implant insertion device and an implant according to a first embodiment.
Figure 2:
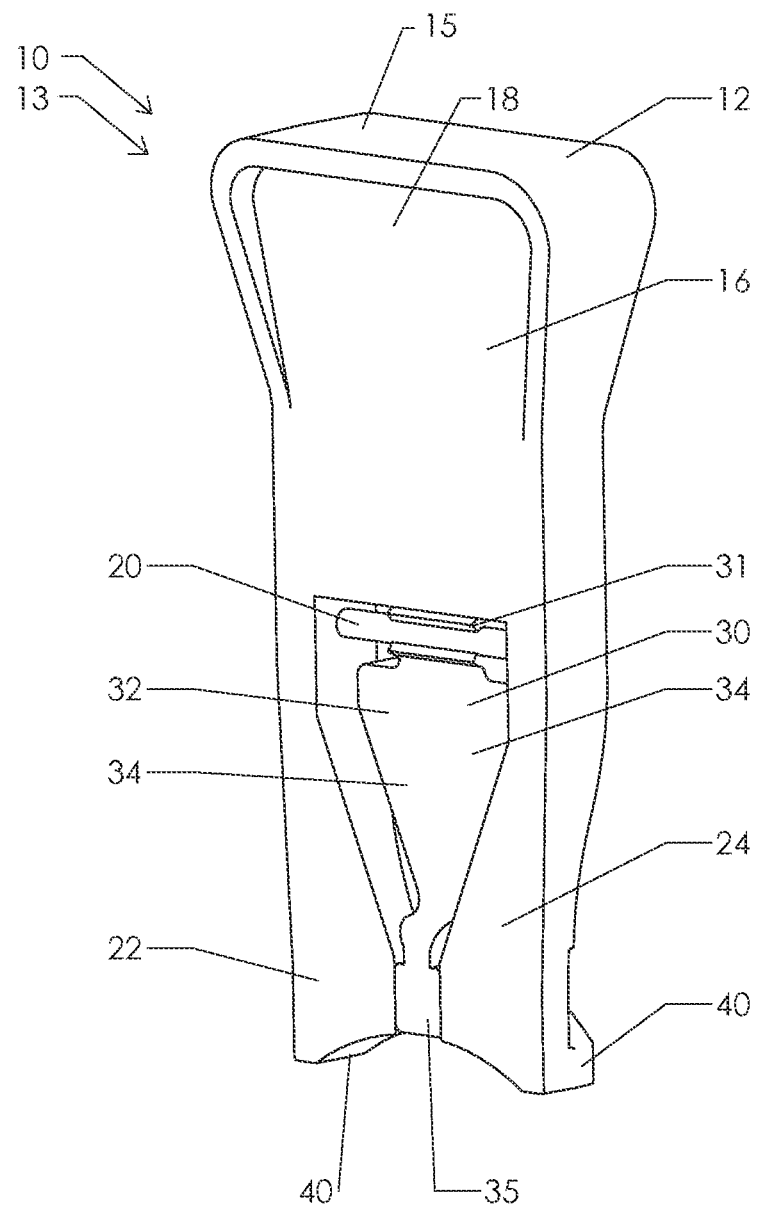
FIG. 2 is a perspective back view illustrating the implant insertion device in an implant engagement position.

FIGS. 1 and 2 are an illustration of a first embodiment of an implant insertion device 10 and an implant 100. The implant 100 secures to the implant insertion device 10 allowing a surgeon to insert the implant 100 into tissue or bone during surgery.

In the first embodiment, the implant 100 is a surgical staple and includes a bridge 120 and legs 130 formed integrally at corners 140. The bridge further 120 includes a top 121, a bottom 122, a back 123, and a front 124. The legs 130 further include tips 131 and bone retention notches 133. The tips 131 of the legs 130 may form a shape that is rounded for insertion into drill holes or the tips 131 may be pointed for impaction into bones. The retention notches 133 are designed to grip tissue or bone and prevent slippage once the implant 100 has been inserted into tissue or bone. While the first embodiment discloses the implant 100 as a surgical staple, it should be understood by one of ordinary skill in the art that any implant such as a staple or plate adapted to engage and span bone such that the implant exerts a force, typically a compressive force, to the bone is suitable for the present invention.

The implant 100 is composed of a shape memory material such as Nitinol that allows the implant 100 to have a first final shape 101 and the ability to be elastically deformed into a second shape 102. The shape memory material gives the implant 100 elastic properties in that the implant 100 stores mechanical energy and is subject to elastic (recoverable) deformation when it releases the stored mechanical energy. The implant 100 is mechanically deformed into the second shape 102 and held in the second shape 102 by the implant insertion device 10 such that, upon release from the implant insertion device 10, the implant 100 elastically transforms from the second shape 102 into the first final shape 101.

The ability of the implant 100 to store mechanical energy and release that energy when it transitions from the second shape 102 to the first final shape 101 allows the implant 100 to fixate tissue or bone and to aid in the healing process. In particular, the implant 100, which has been mechanically deformed to its second shape 102, is held in implant insertion device 10 and inserted between tissue or bone that require fixating. After insertion, the implant 100 is removed from the implant insertion device 10, whereupon the implant 100 releases the stored mechanical energy by elastically deforming to the first final shape 101. This release of the stored mechanical energy by the implant 100 maintains the tissue or bone fixated together and aids in the healing process in that the implant 100 continuously applies force to the fixated tissue or bone as the implant 100 transitions from the second shape 102 to the first final shape 101.

Figure 11:
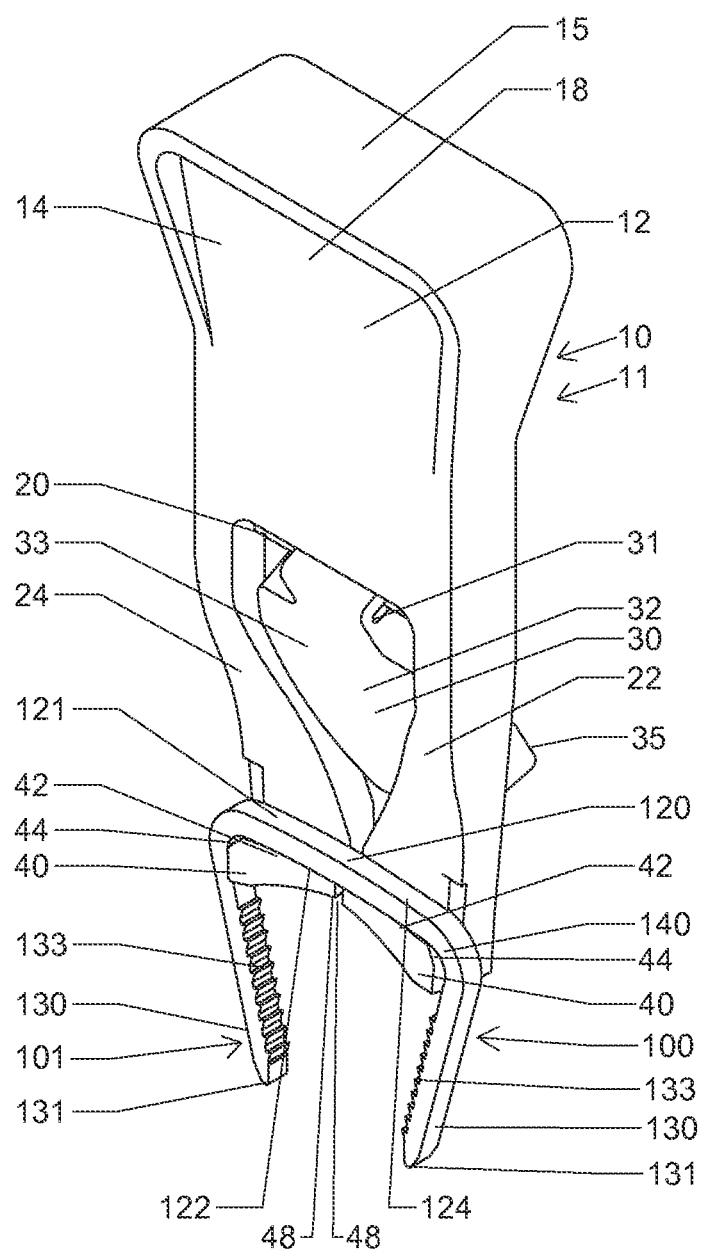
FIG. 11 is a perspective front view illustrating the implant insertion device in the implant disengagement position with an implant positioned for loading on the implant insertion device.
Figure 12:
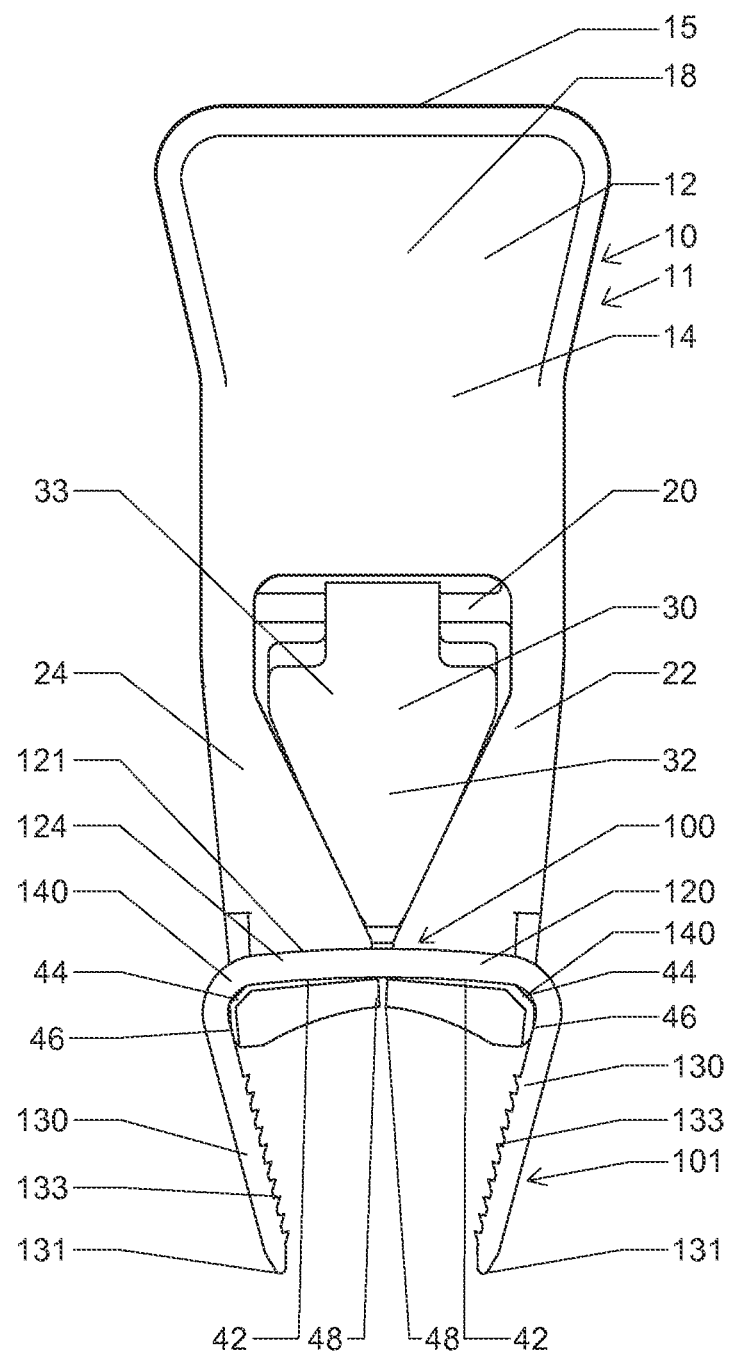
FIG. 12 is a front view illustrating the implant insertion device in the implant disengagement position with an implant positioned for loading on the implant insertion device.
Figure 13:
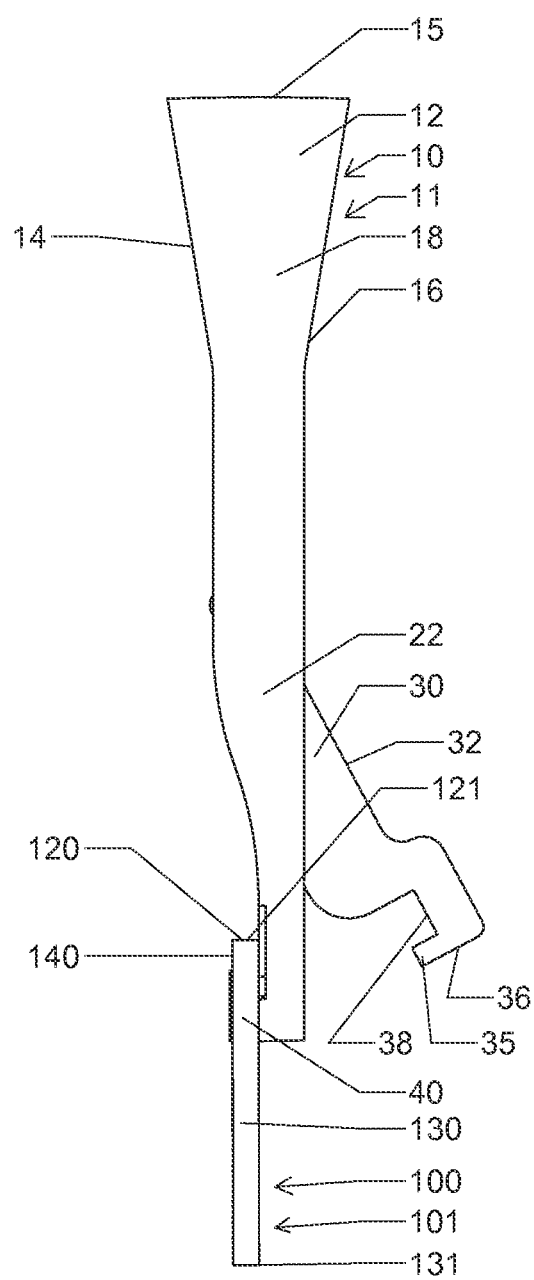
FIG. 13 is a side view illustrating the implant insertion device in the implant disengagement position with an implant positioned for loading on the implant insertion device.
Figure 14:
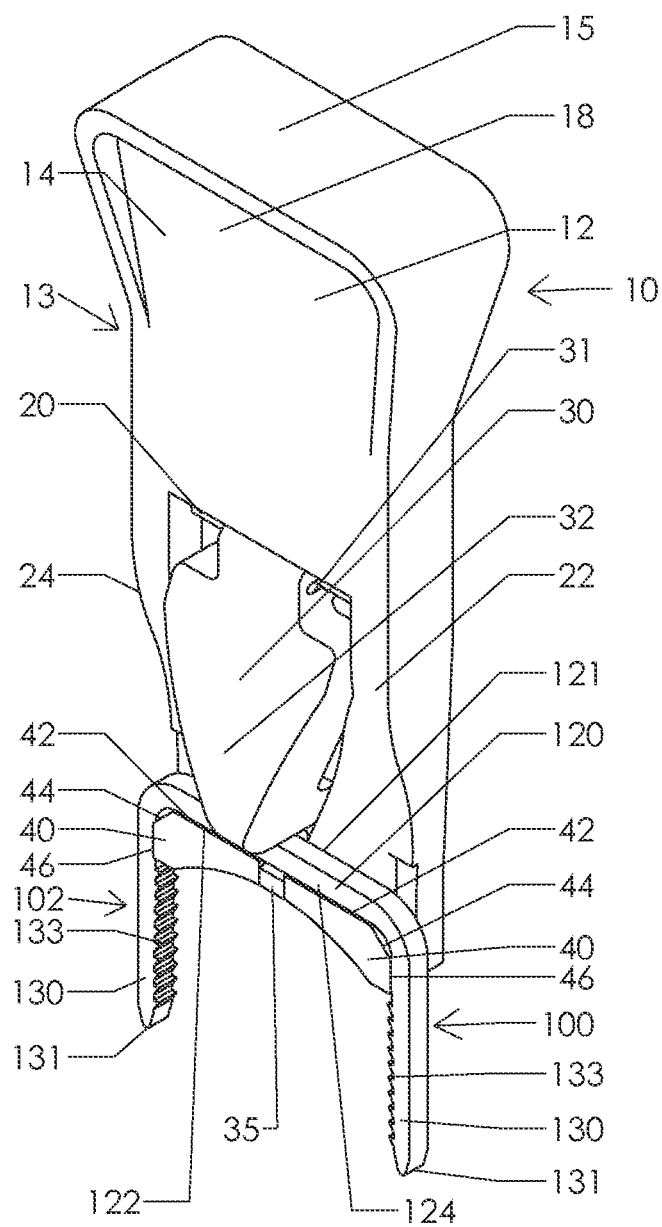
FIG. 14 is a perspective front view illustrating the implant insertion device in the implant engagement position with an implant loaded on the implant insertion device.

The implant insertion device 10 includes a body 12 and a spacer 30. The implant insertion device 10 exists in either an implant disengagement position 11 (shown in FIG. 7) or an implant engagement position 13 (shown in FIG. 3) and is movable therebetween. n the implant disengagement position 11 as shown in FIGS. 11 and 14, the implant 100 slips in or out of position in the implant insertion device 10 with no obstruction. In the implant engagement position 13, the implant 100 is secured in the implant insertion device 10 and maintains the implant 100 in the second shape 102. In addition, the implant insertion device 10 allows a surgeon to manipulate the implant 100 and insert the implant 100 into tissue or bones that require fixating. The implant insertion device 10 can be made of any suitable material; however, in the first embodiment the implant insertion device 10 is made from plastic.

The body 12 of the implant insertion device 10 includes a front 14, a back 16, a handle 18 having a top 15, a pin 20, and arms 22 and 24. The handle 18 provides a gripping surface on the front 14 and the back 16 of the body 12. The gripping surface of the handle 18 allows a surgeon to manipulate the implant insertion device 10 and therefore the implant 100 that is secured thereto. The pin 20 is located below the handle 18 and connects to the arms 22 and 24. The pin 20 is an attachment point for the spacer 30 and allows the spacer 30 to move between a locked position and an unlocked position. The arms 22 and 24 attach to the handle 18 and include jaws 40.

Figure 10:
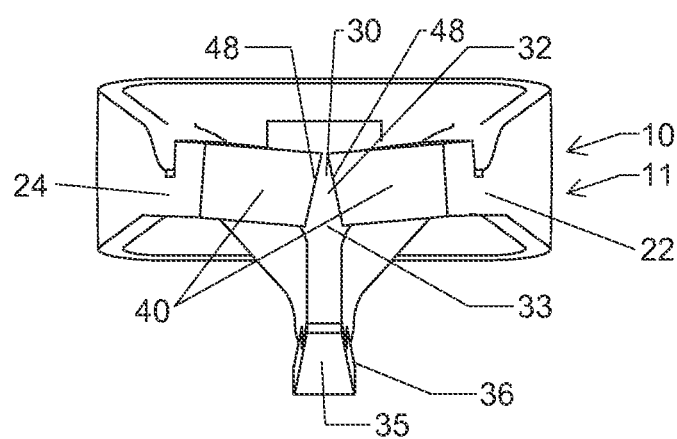
FIG. 10 is a bottom view illustrating the implant insertion device in the implant disengagement position.

The jaws 40 include bridge interfaces 42 and leg interfaces 46. The bridge interfaces 42 and the leg interfaces 46 are formed integrally at corners 44. The jaws 40 further include separator interfaces 48 that engage the spacer 30. The jaws 40 secure the implant 100 to the implant insertion device 10 while also providing easy removal of the implant 100 from the implant insertion device 10. The bottom 122 of the bridge 120 resides atop the bridge interfaces 42 of the jaws 40, while the leg interfaces 46 of the jaws 40 abut the legs 130 below the corners 140. To aid in securing the implant 100 to the implant insertion device 10, the jaws 40 move between an engaged position and an unengaged position. The jaws 40 move to their engaged position when the spacer 30 is moved to its locked position and move to their unengaged position when the spacer 30 is moved to its unlocked position. As shown in FIG. 10, the jaws 40 are rotated away from the spacer in the unengaged position to allow for easier removal of the implant 10 in the unengaged position and prevent entanglement of the jaws and the shape memory implant. The interaction of the spacer 30 with the jaws 40 to move the jaws 40 from their unengaged position to their engaged position will be described in greater detail herein.

The spacer 30 includes a hinge 31, a separator 35, and an actuator 32 having a front face 33 and a back face 34. The hinge 31 snap fits to the pin 20 of the body 12 and allows the spacer 30 to move between its unlocked position and its locked position. The actuator 32 allows a user to operate the spacer 30 by moving the spacer 30 from its unlocked to its locked position. In particular, when the back face 34 of the actuator 32 is pressed, the spacer 30 moves from the unlocked position to the locked position. After reaching the locked position, the user may then press the front face 33 of the actuator 32, which moves the spacer 30 from the locked position to the unlocked position.

The separator 35 defines a space 38 and includes a jaws interface 36. The separator 35 allows the spacer 30 to manipulate the jaws 40 when moving between its unlocked and its locked position. Specifically, when the spacer 30 moves from its unlocked position to its locked position, the separator 35 inserts between the arms 22 and 24 and the jaws 40, thereby moving and forcing the jaws 40 from their unengaged position to their engaged position. In particular, the separator 35 resides between and abuts the arms 22 and 24 and the jaws 40 such that the jaws interface 36 of the separator 35 abuts the separator interfaces 48 of the jaws 40. The separator 35 includes the space 38 to permit travel of the jaws interface 36 past the bridge 120 of the implant 100. As such, the space 38 is larger than the diameter of the bridge 120 such that the separator 35 does not contact the bridge 120.

Inserting the separator 35 between the arms 22 and 24 and the jaws 40 spreads the arms 22 and 24 and the jaws 40 and moves the arms 22 and 24 and the jaws 40 horizontally outward such that the jaws 40 travel to their engaged position whereby the implant 100 is secured to the implant insertion device 10. Furthermore, the arms 22 and 24 when not abutted by the separator 35 maintain the jaws 40 canted downward such that insertion of the separator 35 moves the jaws 40 in an upward arc during engagement of the implant 100 by the jaws 40. For further clarification, the jaws 40 exhibit a rotation (seen to be downward in FIG. 10) relative to arms 22 and 24 when they are not abutted by the separator 35. The jaws 40 accordingly travel outward and upward as well as rotate relative to the arms during engagement with the implant 100. The rotation of the jaws 40 relative to the arms 22 and 24 helps to insure that the jaws more easily disengage without entanglement from the shape memory implant 100 during the disengagement process.

Figure 3:
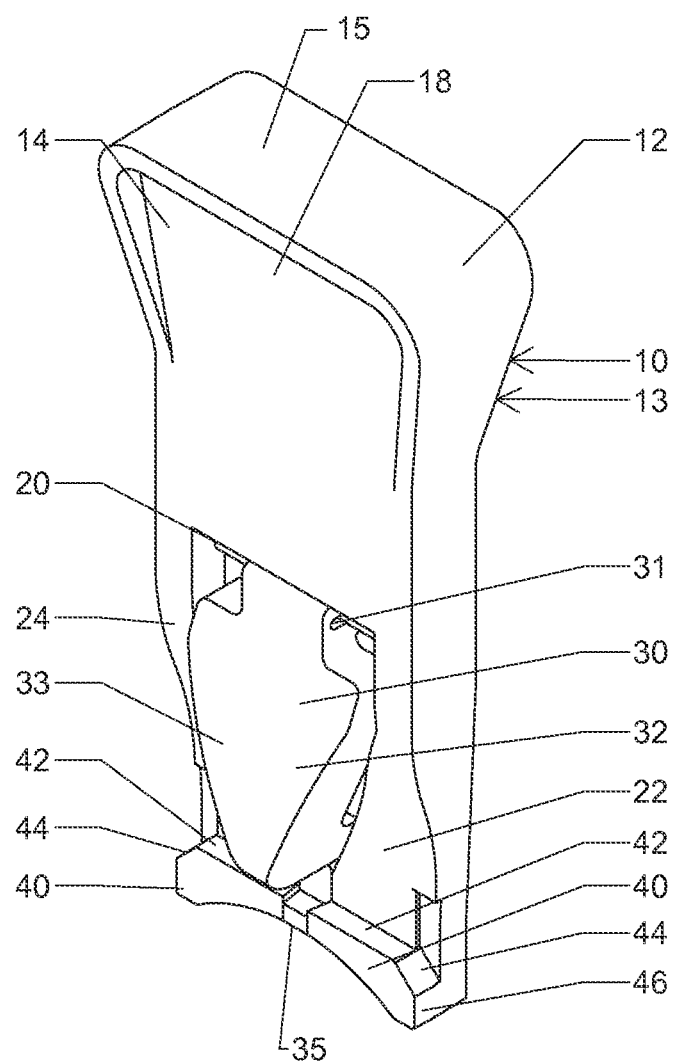
FIG. 3 is a perspective front view illustrating the implant insertion device in the implant engagement position.
Figure 4:
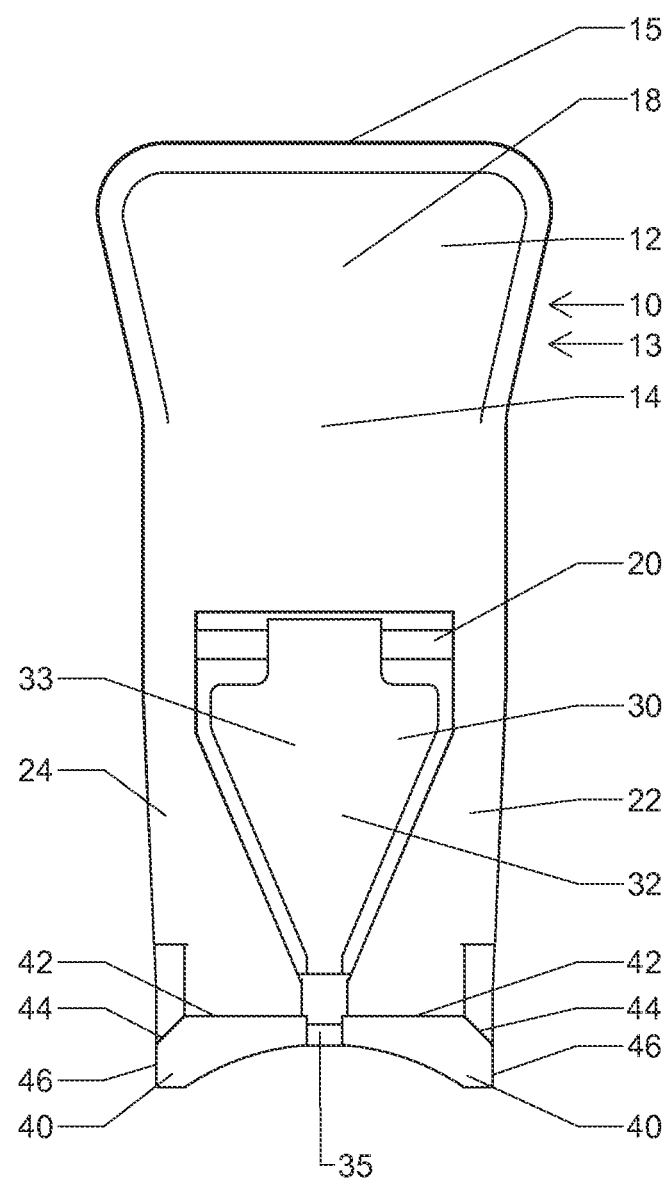
FIG. 4 is a front view illustrating the implant insertion device in the implant engagement position.
Figure 5:
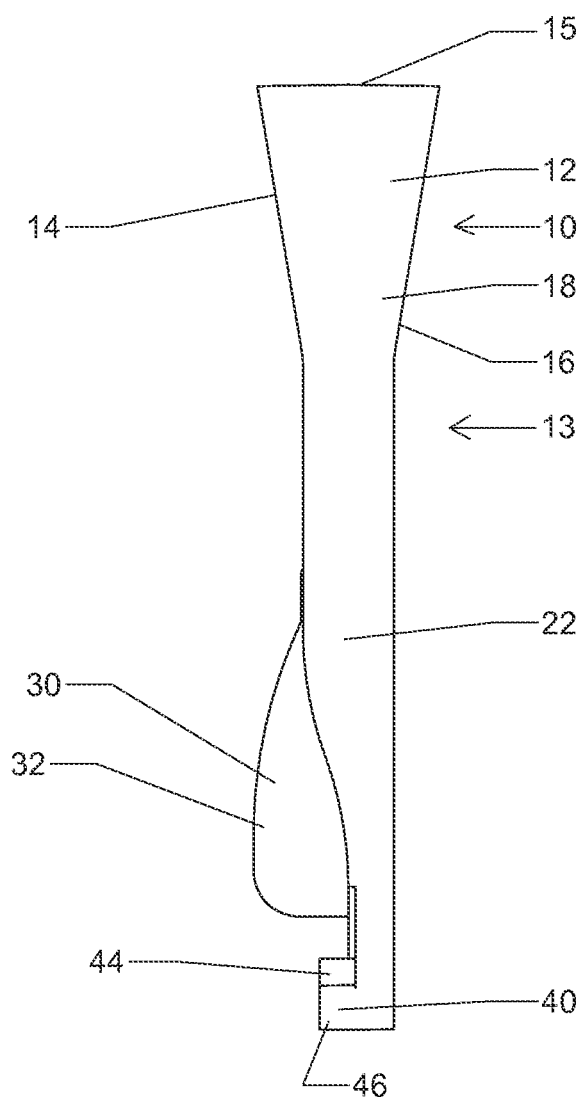
FIG. 5 is a side view illustrating the implant insertion device in the implant engagement position.

FIGS. 3-5 illustrate the spacer 30 in the locked position and the jaws 40 in their engaged position. When the spacer 30 is in the locked position, the jaws interface 36 of the separator 35 abuts the separator interfaces 48 of the jaws 40. In the first embodiment, the separator 35 also engages the arms 22 and 24 to assist in separating the jaws 40 during their engagement of the implant 100. Nevertheless, one of ordinary skill in the art will recognize that only contact between the jaws interface 36 and the separator interfaces 48 are necessary to move the jaws 40 to their engaged position. Alternatively, one of ordinary skill in the art will recognize that the separator 35 contacting only the arms 22 and 24 will move the jaws 40 to their engaged position.

Figure 7:
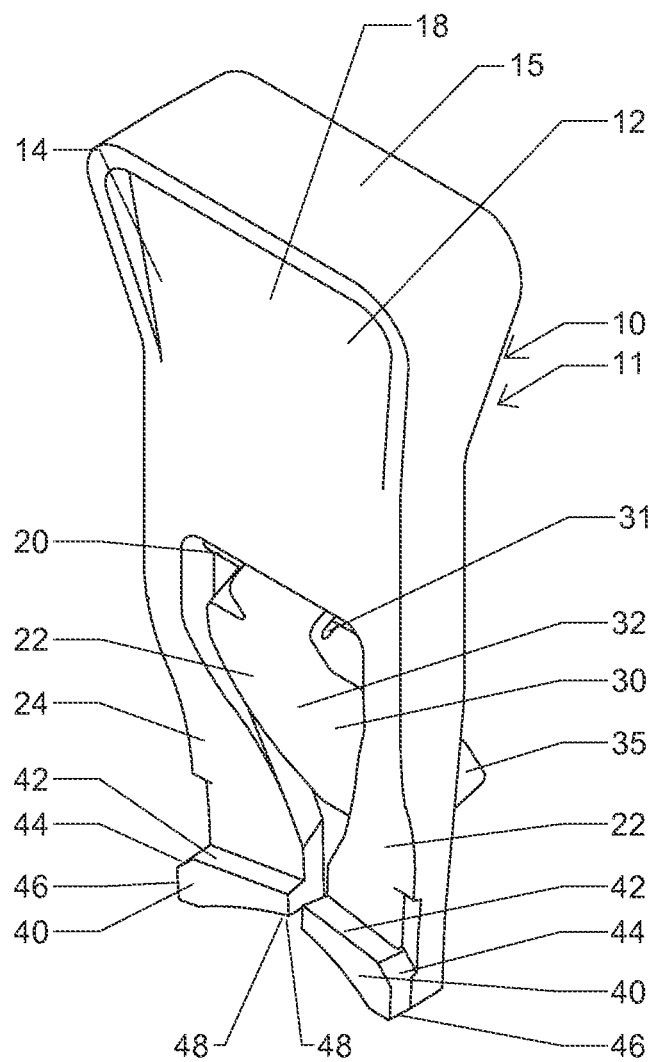
FIG. 7 is a perspective front view illustrating the implant insertion device in an implant disengagement position.
Figure 8:
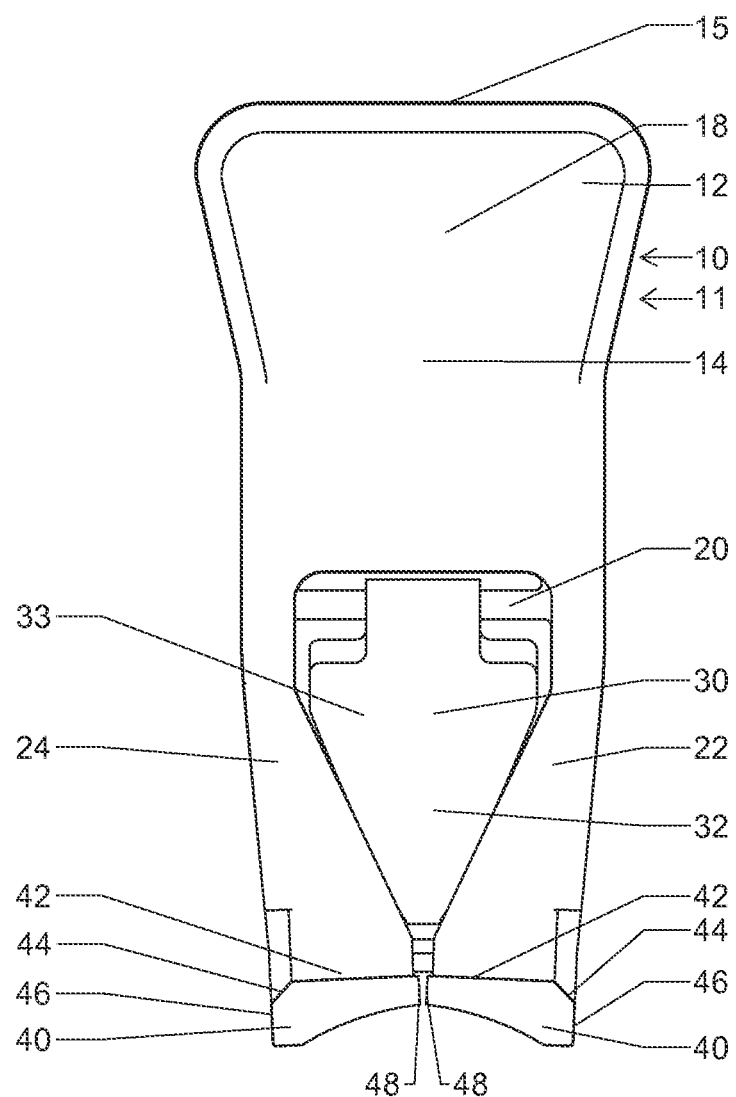
FIG. 8 is a front view illustrating the implant insertion device in the implant disengagement position.
Figure 9:
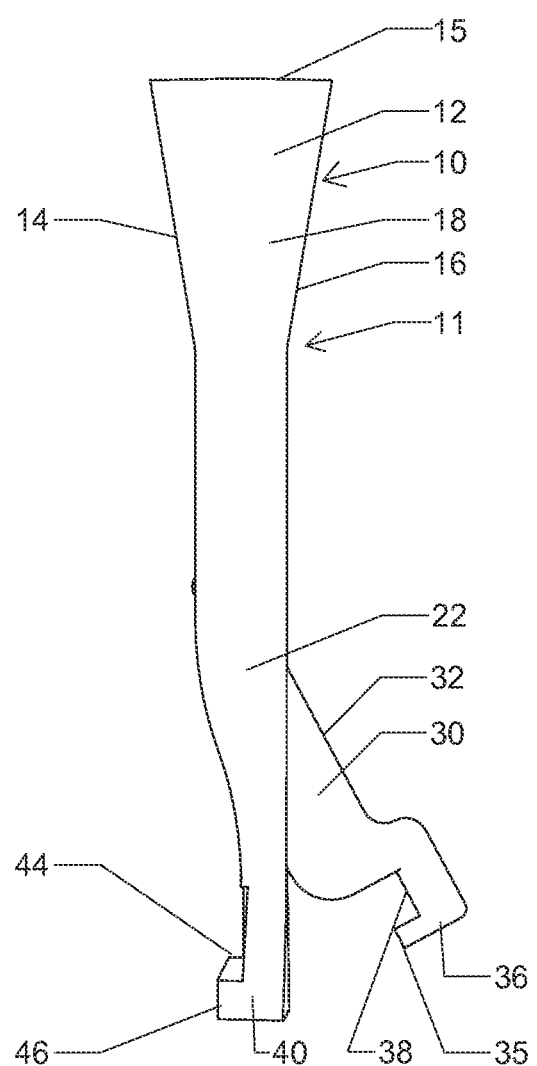
FIG. 9 is a side view illustrating the implant insertion device in the implant disengagement position.

Removing the separator 35 from between the arms 22 and 24 and the jaws 40 releases the arms 22 and 24 and the jaws 40 and allows movement of the arms 22 and 24 and the jaws 40 horizontally inward such that the jaws 40 travel to their unengaged position whereby the implant 100 is released from the implant insertion device 10. The removal of the separator 35 from between the arms 22 and 24 and the jaws 40 further releases the jaws 40 for travel downward in an arc to their downward canted position. The jaws 40 accordingly travel inward and rotate downward during release from the implant 100. FIGS. 7-9 illustrate the spacer 30 in the unlocked position, and the jaws 40 in the unengaged position. When the spacer 30 is in the unlocked position the separator 35 no longer abuts the arms 22 and 24 and the separator interfaces 48 of the jaws 40.

Figure 6:
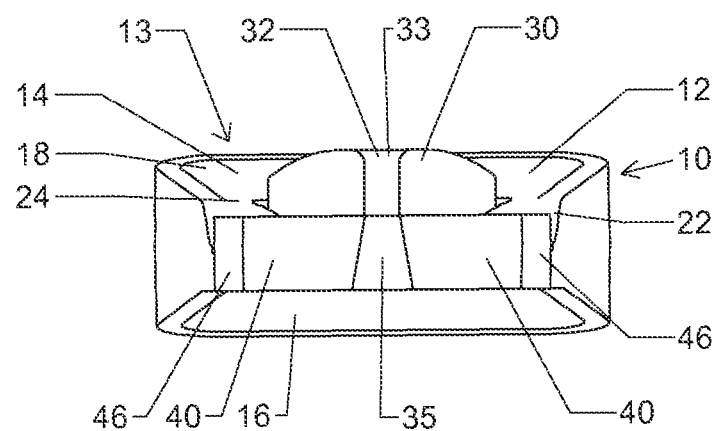
FIG. 6 is a bottom view illustrating the implant insertion device in the implant engagement position.

As illustrated in FIGS. 6 and 10, the separator interfaces 48 of the jaws 40 as well as the jaws interface 36 of the separator 35 are beveled in order to aid in the securing and the removal of the implant 100 from the implant insertion device 10. In the first embodiment, the beveling of the separator interfaces 48 of the jaws 40 and the jaws interface 36 of the separator 35 reduces the normal force between contacting surfaces and thus the friction force between the separator 35 and the jaws 40 as the spacer 30 moves between its locked and its unlocked positions. The beveling of the separator interfaces 48 of the jaws 40 and the jaws interface 36 of the separator 35 also creates a ramp that allows the separator 35 to force open the jaws 40 similar to a wedge when moving from the unlocked to the locked position. One of ordinary skill in the art will recognize that the angle of the bevel and application of trigonometry determines the friction force between the separator 35 and the jaws 40 during the unlocking. Reducing the amount of friction force between the separator 35 and the jaws 40 allows the operator to more easily move the spacer 30 between its locked and unlocked positions, thereby aiding in the removing of the implant 100 from the implant insertion device 10. Furthermore, the angle of the bevel also determines the force for separating the jaws during locking.

FIGS. 11-16 illustrate the operation of securing the implant 100 to the implant insertion device 10 and the removal of the implant 100 from the implant insertion device 10. The implant 100 may be preloaded on the implant insertion device 10 prior to surgery, or the implant 100 may be loaded on the implant insertion device 10 during surgery. The operation of loading the implant 100 on the implant insertion device 10 is as follows.

In a first method to receive the implant 100, the spacer 30 of the implant insertion device 10 is moved to its unlocked position thereby placing the jaws 40 in the unengaged position. The implant 100 is then mechanically deformed from the first final shape 101 into the second shape 102 such that the implant 100 stores mechanical energy. After being mechanically deformed from the first final shape 101 into the second shape 102, the implant 100 is placed over the jaws 40 of the implant insertion device 10. The implant 100 is then placed over the jaws 40 such that the bottom 122 of the bridge 120 resides adjacent the bridge interfaces 42 and the back 123 resides adjacent the arms 22 and 24 of the body 12.

Figure 15:
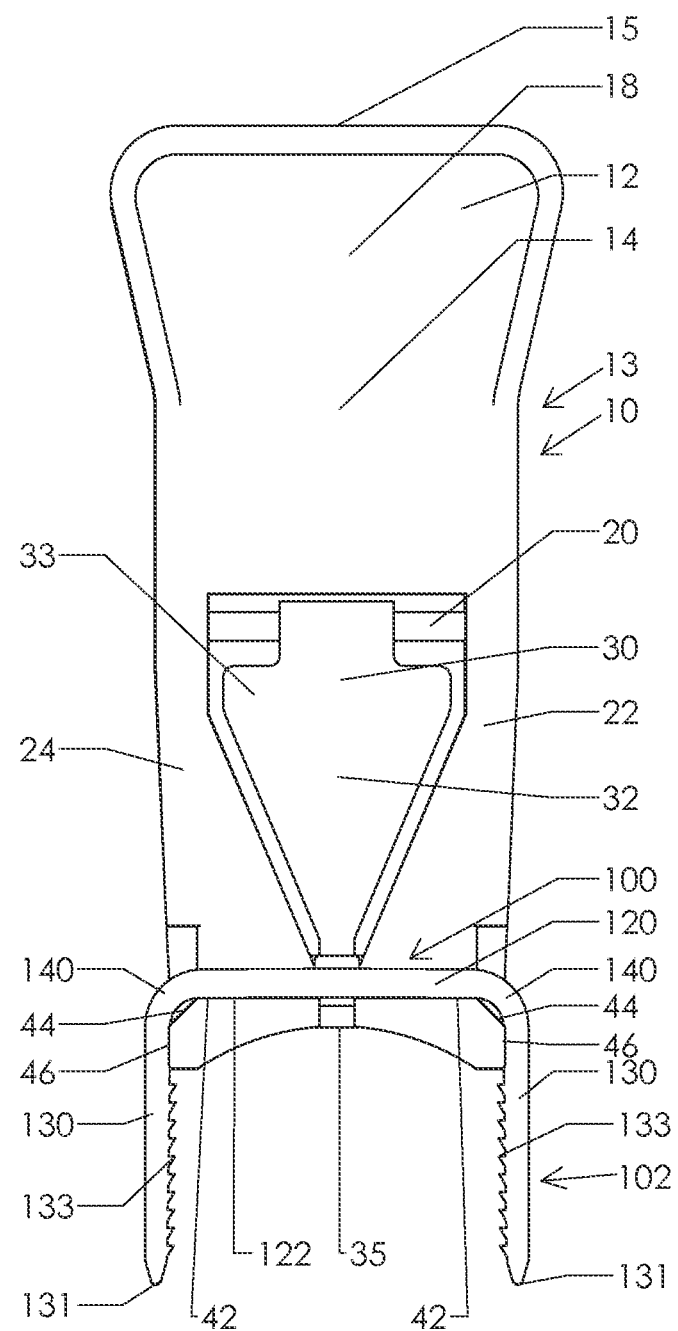
FIG. 15 is a front view illustrating the implant insertion device in the implant engagement position with an implant loaded on the implant insertion device.
Figure 16:
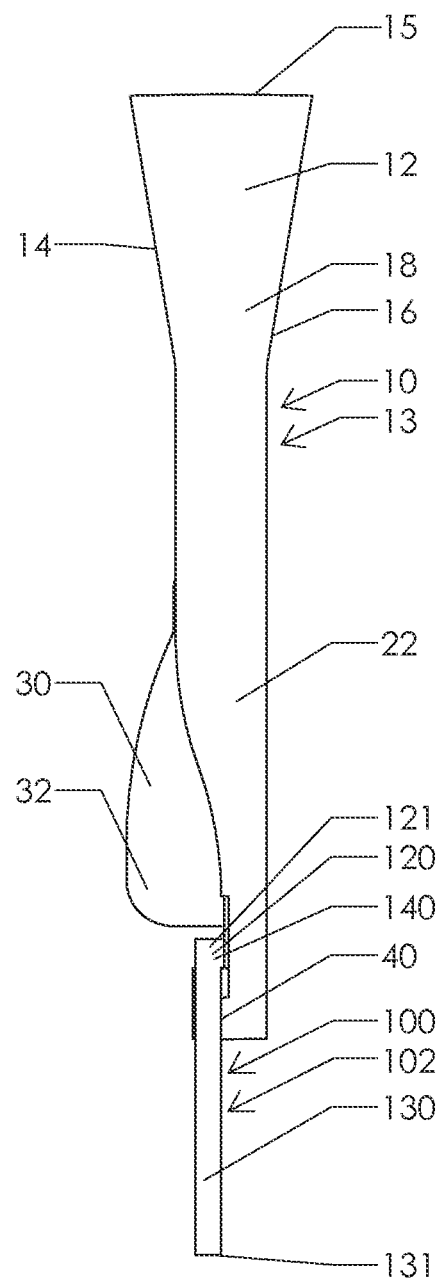
FIG. 16 is a side view illustrating the implant insertion device in the implant engagement position with an implant loaded on the implant insertion device.

After the implant 100 is placed over the jaws 40, the spacer 30 of the implant insertion device 10 is moved from its unlocked position into its locked position. As the spacer 30 moves from its unlocked position to its locked position, the jaw interfaces 36 of the separator 35 abut the jaws 40 at the separator interfaces 48. The engagement of the separator 35 with the jaws 40 moves the leg interfaces 46 of the jaws 40 horizontally outward and upward in an arc towards the legs 130 of the implant 100, while at the same time rotating the jaws 40 to engage the legs 130. As illustrated in FIGS. 14-16, when the spacer 30 is in its locked position, the leg interfaces 46 of the jaws 40 will abut the legs 130 below the corners 140 of the implant 100, and the jaws 40 will be moved and rotated to their engaged position, thereby securing the implant 100 to the implant insertion device 10. In particular, the mechanical energy stored in the implant 100 tensions the implant 100 against the jaws 40 such that the implant 100 remains loaded on the implant insertion device 10 while the implant insertion device 10 also maintains the implant 100 in the second shape 102.

While the implant 100 may be mechanically deformed from the first final shape 101 into its second shape 102 before placement on the implant insertion device 10, in a second method, the implant 100 also may be placed on the implant insertion device 10 in the first final shape 101 and then mechanically deformed to the second shape 102 by the implant insertion device 10. As the spacer 30 of the implant insertion device 10 is moved from its unlocked position to its locked position, the spacer 30 will engage the jaws 40, thereby moving the jaws 40 from their unengaged to their engaged position. The force of the spacer 30 moving and rotating the jaws 40 will be transferred to the implant 100 such that the implant 100 moves from its first final shape 101 to the second shape 102. This force transfer imparts mechanical energy into the implant 100 and tensions the implant 100 against the jaws 40 such that the implant 100 remains loaded on the implant insertion device 10 while the implant insertion device 10 also maintains the implant 100 in the second shape 102. Although not necessary, the implant 100 may be cooled prior to placement on the implant insertion device 10 in order to place it in a martensitic state and aid in movement of the implant 100 from its first final shape 101 to the second shape 102.

Figure 17:
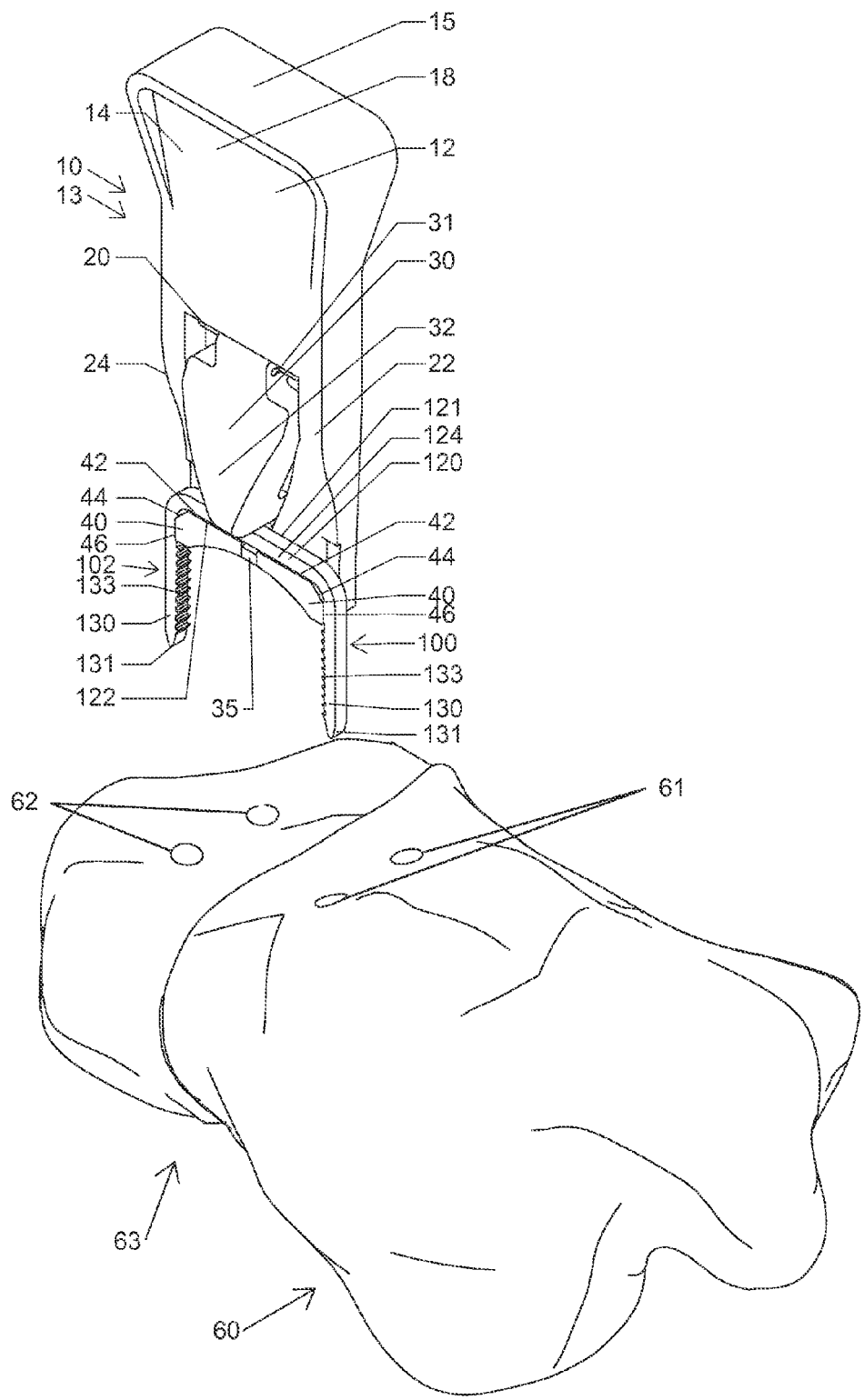
FIG. 17 is a perspective front view illustrating the implant insertion device in the engagement position with an implant loaded on the implant insertion device positioned for loading into bone.
Figure 18:
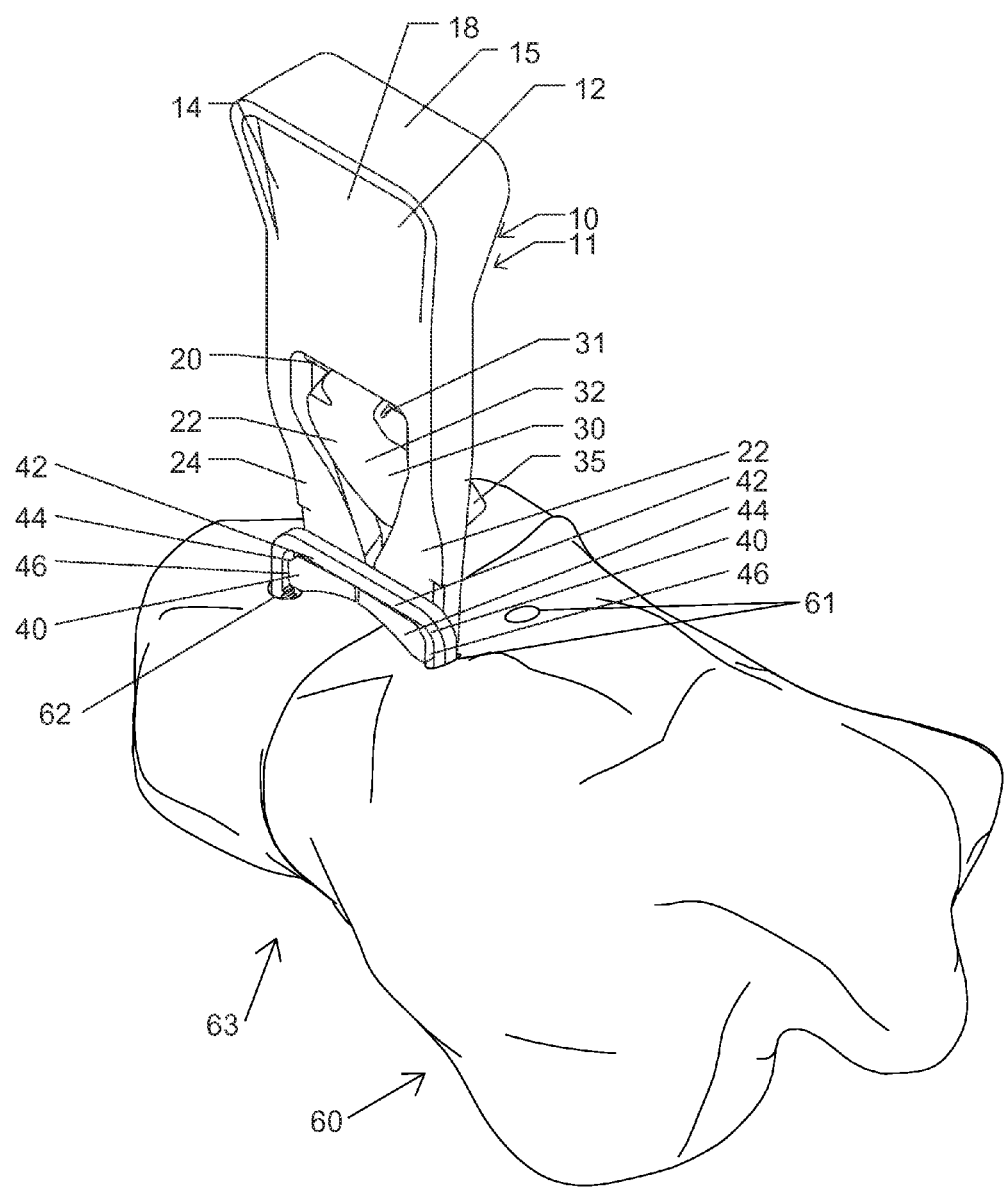
FIG. 18 is a perspective front view illustrating the implant insertion device in the disengagement position with the implant inserted into bone.
Figure 19:
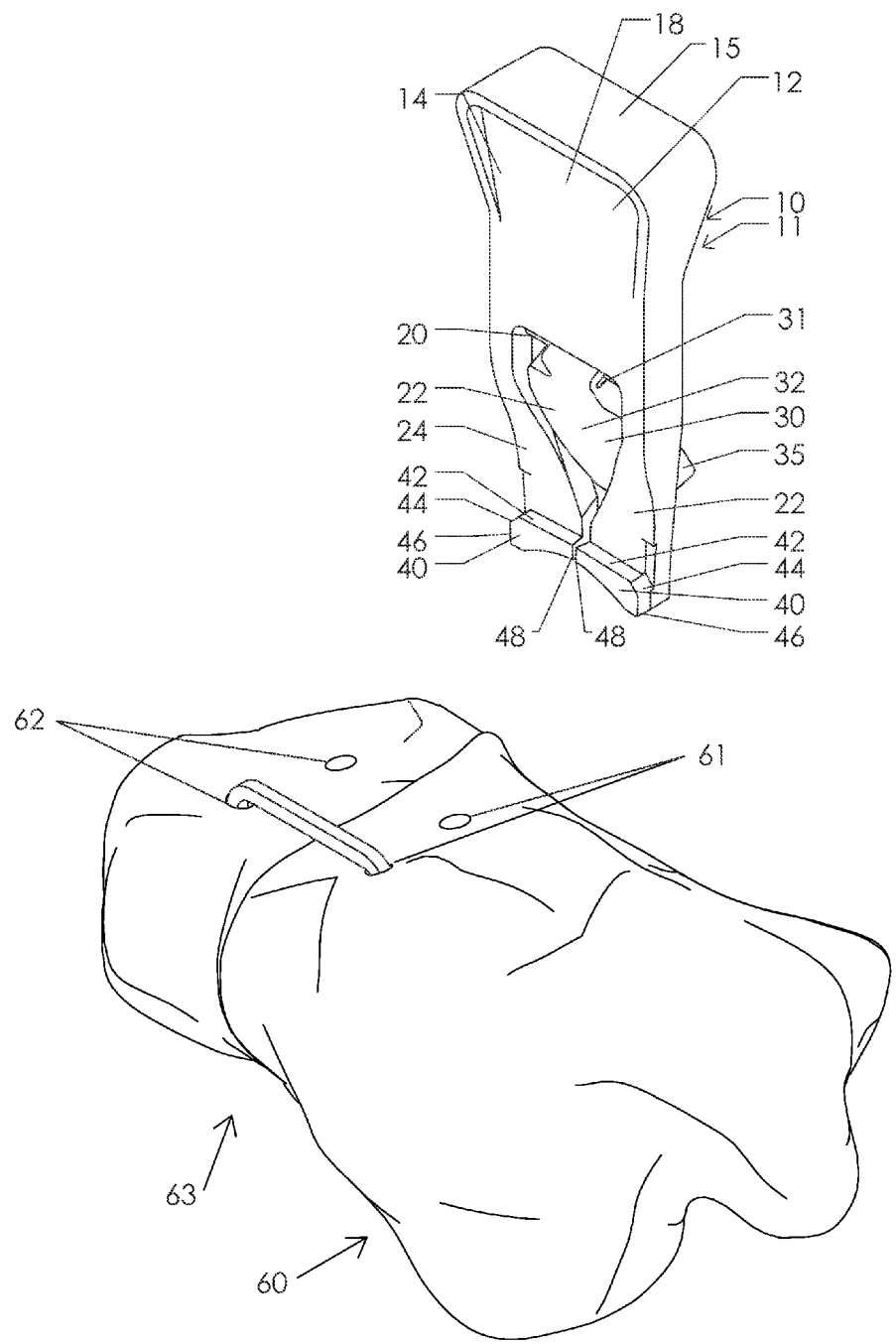
FIG. 19 is a perspective front view illustrating the implant insertion device in the disengagement position with the implant fully inserted into bone.
Figure 20:
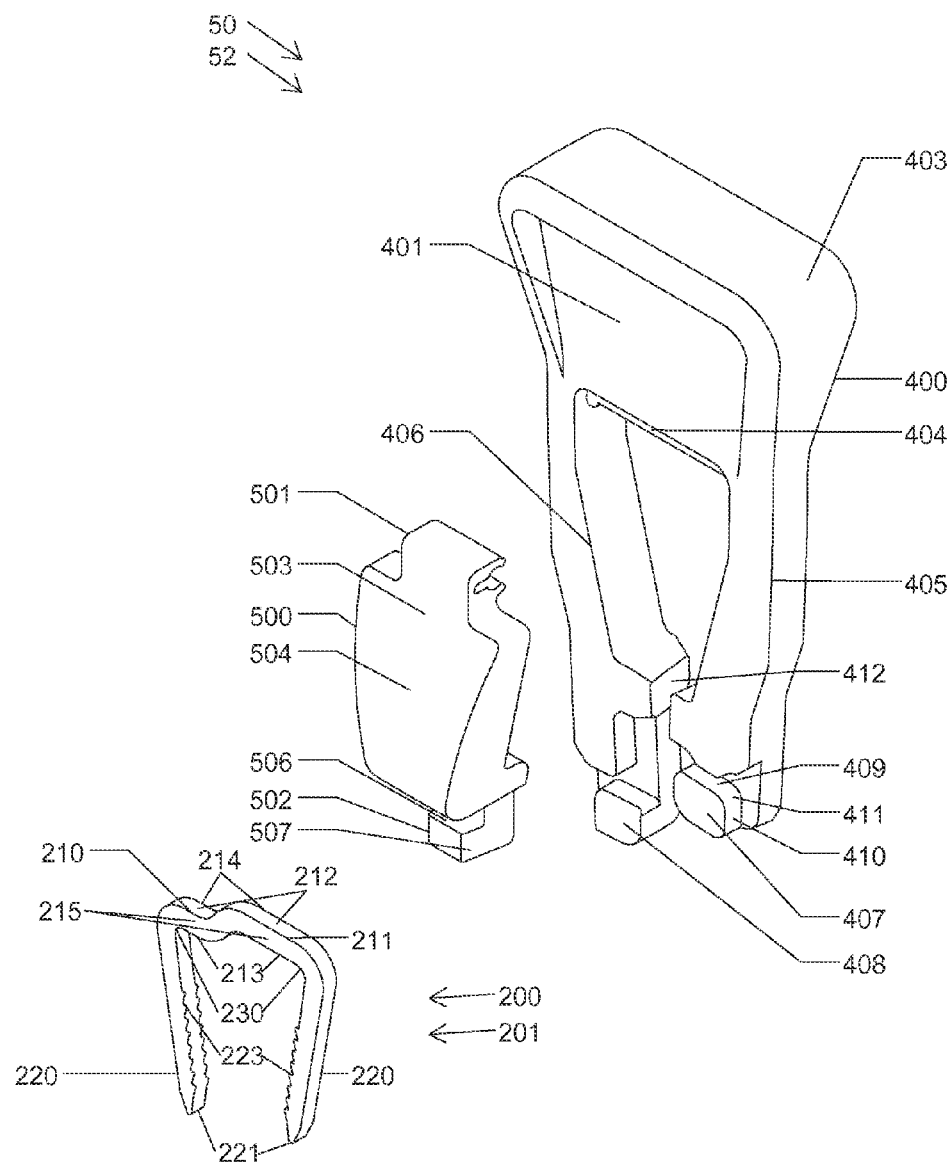
FIG. 20 is a perspective exploded front view illustrating a body and spacer of an implant insertion device and an implant according to a second embodiment.
Figure 21:
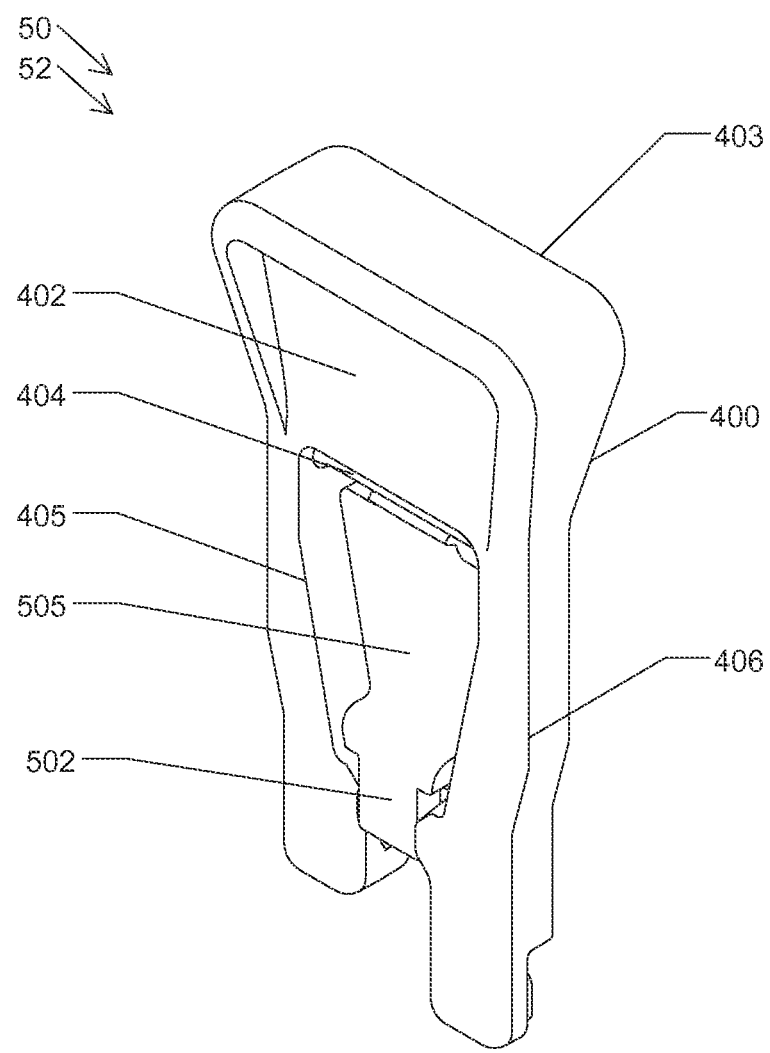
FIG. 21 is a perspective back view of the implant insertion device in an implant engagement position.
Figure 22:
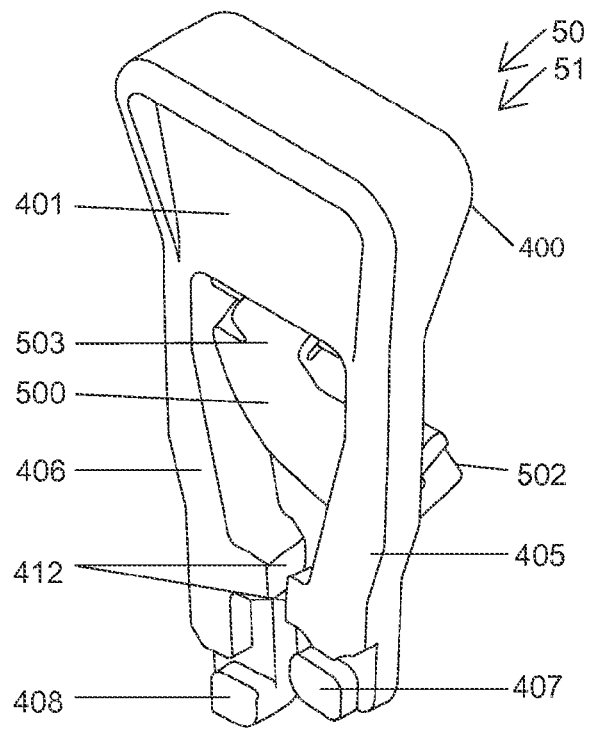
FIG. 22 is a perspective front view illustrating the implant insertion device in an implant disengagement position.

After the implant 100 is secured to the implant insertion device 10, the implant 100 is ready to be implanted into tissue or bones 60 and 63 as shown in FIG. 17. The surgeon places the tips 131 of the implant 100 into predrilled holes 61 and 62 or the tips may be impacted into the tissue or bones 60 and 63 thereby securing the implant 100 into the tissue or bones 60 and 63. Once the implant 100 is secured to the tissue or bones 60 and 63, it is ready for removal from the implant insertion device 10. To remove the implant 100 from the implant insertion device 10, the surgeon presses the actuator 32 at the front 33 of the spacer 30 at the rate desired by the surgeon. Pressing the actuator 32 at the front 33 of the spacer 30 moves the spacer 30 from its locked position to its unlocked position as shown in FIG. 18. The rate of movement of spacer 30 is controlled by the surgeon pressing the actuator 32. If the surgeon presses actuator 32 quickly, then the spacer 30 moves from its locked to its unlocked position quickly. On the other hand, if the surgeon believes a patient has poor bone quality, the surgeon can slowly presses the actuator 32, which slowly moves the spacer 30 from the locked to the unlocked position. As the spacer 30 moves from its locked position to its unlocked position, the jaws interface 36 of the separator 35 disengages the jaws 40 at the separator interfaces 48. The disengagement of the separator 35 with the jaws 40 moves the jaws 40 from their engaged position to their unengaged position in that the leg interfaces 46 of the jaws 40 move horizontally inward and downward in an arc away from the legs 130 of the implant 100. To further clarify the downward arcing motion, the jaws 40 rotate away from legs 130 to avoid entanglement with legs 130. Movement of the jaws 40 both horizontally inward and downward in an arc away from the legs 130 of the implant 100 enhances and simplifies separation of the implant insertion device 10 from the implant 100. When the spacer 30 is in its unlocked position and the jaws 40 are in their unengaged position, the leg interfaces 46 no longer abut the legs 130 of the implant 100, and in fact are angled away from legs 130, resulting in the release of the tension between the implant 100 and the jaws 40. The implant 100 accordingly no longer contacts and is no longer secured to the implant insertion device 10, thus allowing the removal of the implant 100 from the implant insertion device 10 as shown in FIG. 19.

In addition to the above-described method of removing the implant 100 from the implant insertion device 10, the implant 100 may be removed from the implant insertion device 10 by applying a twisting force to the implant insertion device 10. Specifically, after the tips 131 of the legs 130 are inserted into the tissue or bones 60 and 63, as illustrated in FIG. 18, the surgeon applies a twisting or rotational force to the implant insertion device 10 relative to the implant 100. The twisting or rotational force overcomes the force the jaws 40 apply against the implant 100. As a result, the jaws 40 separate from the implant 100, thereby releasing the implant 100 from the implant insertion device 10. In particular, the leg interfaces 46 of the jaws 40 separate from the legs 130 of the implant 100 such that the implant insertion device 10 is removed from the implant 100 as illustrated in FIG. 19.

Removing the implant 100 from the implant insertion device 10 using a twisting or rotational force is possible due to the minimized contact between the implant 100 and the implant insertion device 10 when the implant 100 is secured to the implant insertion device 10. As described above, when the implant 100 is secured to the implant insertion device 10, the main contact point between the implant insertion device 10 and the implant 100 exists at the leg interfaces 46 of the jaws 40 and the legs 130. Accordingly, there is no contact between the top 121 and the front 124 of the bridge 120 and when the spacer 30 is in its locked position. As such, only the force the jaws 40 apply against the implant 100 must be overcome in order for the implant 100 to be released from the implant insertion device 10. This minimizes the twisting or rotational force required for the release of the implant 100, thereby simplifying the removal of the implant 100 from the implant insertion device 10.

After the implant 100 is removed from the implant insertion device 10, the implant 100 is tamped down to fully engage the tissue or bones 60 and 63. Once fully engaged, the implant 100 moves from its second shape 102 to its first final shape 101, thereby releasing its mechanical energy into the tissue or bones 60 and 63. As the implant 100 moves from its second shape 102 to its first final shape 101, the implant 100 places a constant force on the tissue or bones 60 and 63 that fuses the tissue or bone 60 and 63 together and aids the healing process.

FIGS. 20-31 are an illustration of a second embodiment of an implant insertion device 50 and an implant 200. The implant 200 is secured to the implant insertion device 50 allowing a surgeon to insert the implant 200 into tissue or bone during surgery.

In the second embodiment, the implant 200 is a surgical staple and includes two bridges 210 and 211 and legs 220 formed integrally at corners 230. The bridges 210 and 211 each include a top 212, a bottom 213, a back 214, and a front 215. The legs 220 further include tips 221 and bone retention notches 223. The tips 221 of the legs 220 may form a shape that is rounded for insertion into drill holes or the tips 221 may be pointed for impaction into bones. The retention notches 223 are designed to grip tissue or bone and prevent slippage once the implant 200 has been inserted into tissue or bone. While the second embodiment discloses the implant 200 as a surgical staple, it should be understood by one of ordinary skill in the art that any implant adapted to engage and span bone such that the implant exerts a force, typically a compressive force, to the bone is suitable for the present invention.

The implant 200 is composed of a shape memory material such as Nitinol that allows the implant 200 to have a first shape 201 and the ability to transform into a second shape 202. The shape memory material gives the implant 200 elastic properties in that the implant 200 stores mechanical energy and is subject to elastic (recoverable) deformation when it releases the stored mechanical energy. The implant 200 is mechanically deformed into the second shape 202 and held in the second shape 202 by the implant insertion device 50 such that, upon release from the implant insertion device 50, the implant 200 elastically deforms from the second shape 202 into the first shape 201.

As illustrated in FIGS. 20-31, the implant insertion device 50 includes a body 400 and a spacer 500. The implant insertion device 50 has a disengagement position 51 and an implant engagement position 52. In the implant disengagement position 51 as illustrated in FIGS. 22-25, the implant 200 slips in or out of position in the implant insertion device 50 with no obstruction. In the implant engagement position 52 as illustrated in FIGS. 26-31, the implant insertion device 50 secures the implant 200 and maintains the implant 200 in the second shape 202. In addition, the implant insertion device 50 allows a surgeon to manipulate the implant 200 and insert the implant 200 into tissue or bone requiring fixating. The implant insertion device 50 can be made of any suitable material; however, in the second embodiment the implant insertion device 50 is made from plastic.

The body 400 of the implant insertion device 50 includes a front 401, a back 402, a handle 403, a pin 404, an arm 405, and an arm 406. The handle 403 provides a gripping surface on the front 401 and the back 402 of the body 400 allowing a surgeon to manipulate the implant insertion device 50 and therefore the implant 200 that is secured thereto. The pin 404 is located below the handle 403 and connects between the arms 405 and 406. The pin 404 provides an attachment point for the spacer 500 and allows the spacer 500 to move between a locked and unlocked position. The arms 405 and 406 attach to the handle 403 and include jaws 408 and 407, respectively. The arm 406 is shorter in length than the arm 405 to accommodate the difference in bridge height of the staple implant 200. The arms 405 and 406 are designed to be flexible if an external force is applied thereto. One of ordinary skill in the art will recognize that the arms 405 and 406 can be at many relative angles from each other. One skilled in the art will further recognize that the length and height difference of the arms 405 and 406 may vary to deliver a variety of results.

The jaws 407 and 408 include bridge interfaces 409 and leg interfaces 410. The bridge interfaces 409 and the leg interfaces 410 are formed integrally at corners 411. In the second embodiment, the jaws 407 and 408 each include a stop 415 located above the bridge interfaces 409 that along with the bridge interfaces 409 define a slot that receives therein at least a portion of the bridges 210 and 211, respectively. The jaws 407 and 408 further include separator interfaces 412 that engage the spacer 500. The jaws 407 and 408 secure the implant 200 to the implant insertion device 50 while also providing easy removal of the implant 200 from the implant insertion device 50. For implant 200, at least a portion of the bottoms 213 of the bridges 210 and 211 resides atop the bridge interfaces 409 of the jaws 407 and 408, at least a portion of the tops 215 of the bridges 210 and 211 resides adjacent the stops 415 of the jaws 407, and the leg interfaces 410 of the jaws 407 and 408 abut the legs 220 below the corners 230. To aid in securing the implant 200 to the implant insertion device 50, the jaws 407 and 408 move between an unengaged position and an engaged position such that the implant insertion device 50 travels between its disengagement position 51 and its implant engagement position 52. The jaws 407 and 408 travel to their engaged position when the spacer 500 moves to its locked position. Likewise, the jaws 407 and 408 travel to their unengaged position when the spacer 500 moves to its unlocked position.

The spacer 500 includes a hinge 501, a separator 502, and an actuator 503 having a front face 504 and a back face 505. The hinge 501 snap fits to the pin 404 of the body 400 and allows the spacer 500 to move between its unlocked position and its locked position. The actuator 503 allows the surgeon to operate the spacer 500 by moving the spacer 500 from its unlocked to its locked position. In particular, when a user presses the back face 505 of the actuator 503 the spacer 500 moves from the unlocked position to the locked position. After reaching the locked position, the surgeon may press the front face 504 of the actuator 503, which moves the spacer 500 from the locked position to the unlocked position.

The separator 502 defines a space 506 and includes a jaws interface 507. The separator 502 allows the spacer 500 to manipulate the jaws 407 and 408 when moving between its unlocked and its locked position. Specifically, when the spacer 500 moves from its unlocked position to its locked position, the separator 502 inserts between the arms 405 and 406 and engages the jaws 407 and 408, thereby moving the jaws 407 and 408 from their unengaged position to their engaged position. In particular, the separator 502 resides between and abuts the jaws 407 and 408 such that the jaws interface 507 of the separator 502 abuts the separator interfaces 412 of the jaws 407 and 408.

Inserting the separator 502 between the jaws 407 and 408 spreads the arms 405 and 406 and the jaws 407 and 408, thereby moving the arms 405 and 406 and the jaws 407 and 408 horizontally outward such that the jaws 407 and 408 travel to their engaged position whereby the implant 200 is secured to the implant insertion device 50. Furthermore, when the separator 502 does not abut the jaws 407 and 408, the arms 405 and 406 maintain the jaws 407 and 408 canted downward such that insertion of the separator 502 moves the jaws 407 and 408 in an upward arc during engagement of the implant 200 by the jaws 407 and 408. The jaws 407 and 408 accordingly travel outward and upward during engagement with the implant 200.

FIGS. 28-31 illustrate the spacer 500 in the locked position and the jaws 407 and 408 in their engaged position. When the spacer 500 is in the locked position, the jaws interface 507 of the separator 502 abuts the separator interfaces 412 of the jaws 407 and 408. In the second embodiment, the separator 502 engages only the separator interfaces 412 of the jaws 407 and 408. Nevertheless, one of ordinary skill in the art will recognize that the separator 502 may also engage the arms 405 and 406 to assist in separating the jaws 407 and 408 during their engagement of the implant 200 Alternatively, one of ordinary skill in the art will recognize that the separator 502 contacting only the arms 405 and 406 will move the jaws 407 and 408 to their engaged position.

Removing the separator 502 from between the arms 405 and 406 and the jaws 407 and 408 releases the arms 405 and 406 and the jaws 407 and 408 and allows movement of the arms 405 and 406 and the jaws 407 and 408 horizontally inward such that the jaws 407 and 408 travel to their unengaged position whereby the implant 200 is released from the implant insertion device 50. The removal of the separator 502 from between the arms 405 and 406 and the jaws 407 and 408 further releases the jaws 407 and 408 for travel downward in an arc to their downward canted position. The jaws 407 and 408 accordingly travel inward and downward during release from the implant 200. FIGS. 22-25 illustrate the spacer 500 in the unlocked position, and the jaws 407 and 408 in the unengaged position. When the spacer 500 is in the unlocked position the separator 502 no longer abuts the separator interfaces 412 of the jaws 407 and 408.

Figure 23:
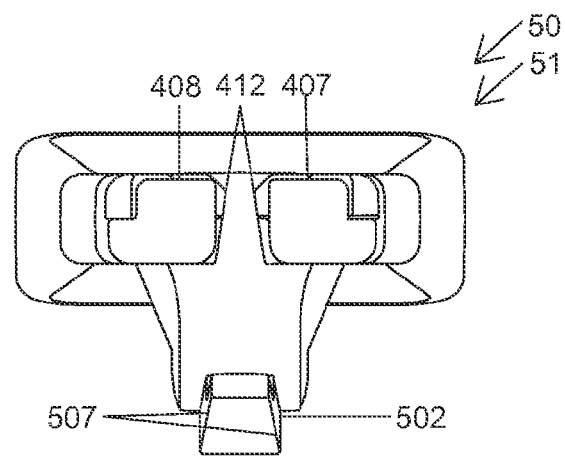
FIG. 23 is a bottom view illustrating the implant insertion device in the implant disengagement position.
Figure 29:
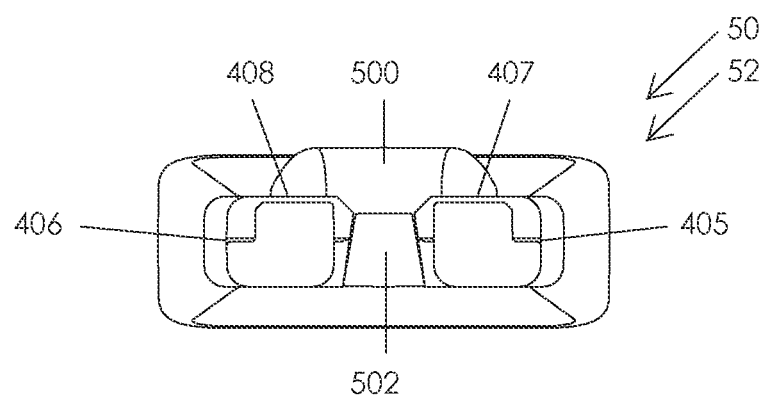
FIG. 29 is a bottom view illustrating the implant insertion device in the implant engagement position.
Figure 30:
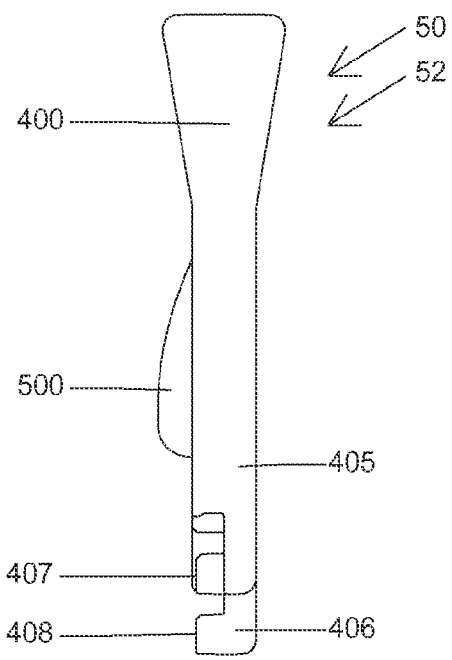
FIG. 30 is a left side view illustrating the implant insertion device in the implant engagement position.
Figure 31:
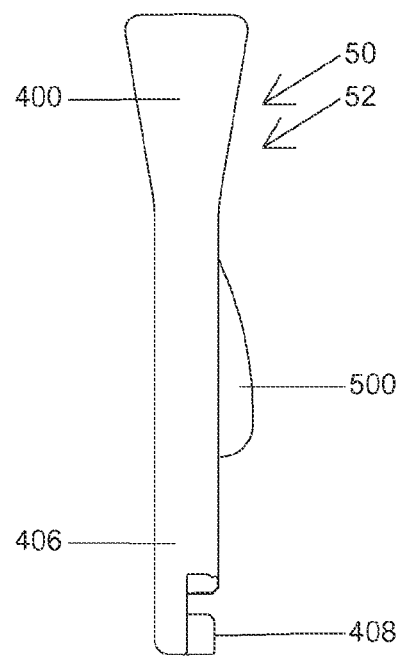
FIG. 31 is a right side view illustrating the implant insertion device in the implant engagement position.

As illustrated in FIGS. 23 and 29, the separator interfaces 412 of the jaws 407 and 408 as well as the jaws interface 507 of the separator 502 are beveled in order to aid in the securing and the removal of the implant 200 from the implant insertion device 50. In the second embodiment, the beveling of the separator interfaces 412 of the jaws 407 and 408 and the jaws interface 507 of the separator 502 reduces the amount of surface area for contact and thus the friction force between the separator 502 and the jaws 407 and 408 as the spacer 500 moves between its unlocked and its locked positions. One of ordinary skill in the art will recognize that the angle of the bevel controls the amount of surface area for contact and thus the friction force between the separator 502 and the jaws 407 and 408. Reducing the amount of friction force between the separator 502 and the jaws 407 and 408 allows the operator to more easily move the spacer 500 between its unlocked and locked positions, thereby aiding in the securing of the implant 200 to the implant insertion device 50 as well as the removing of the implant 200 from the implant insertion device 50.

Figure 32:
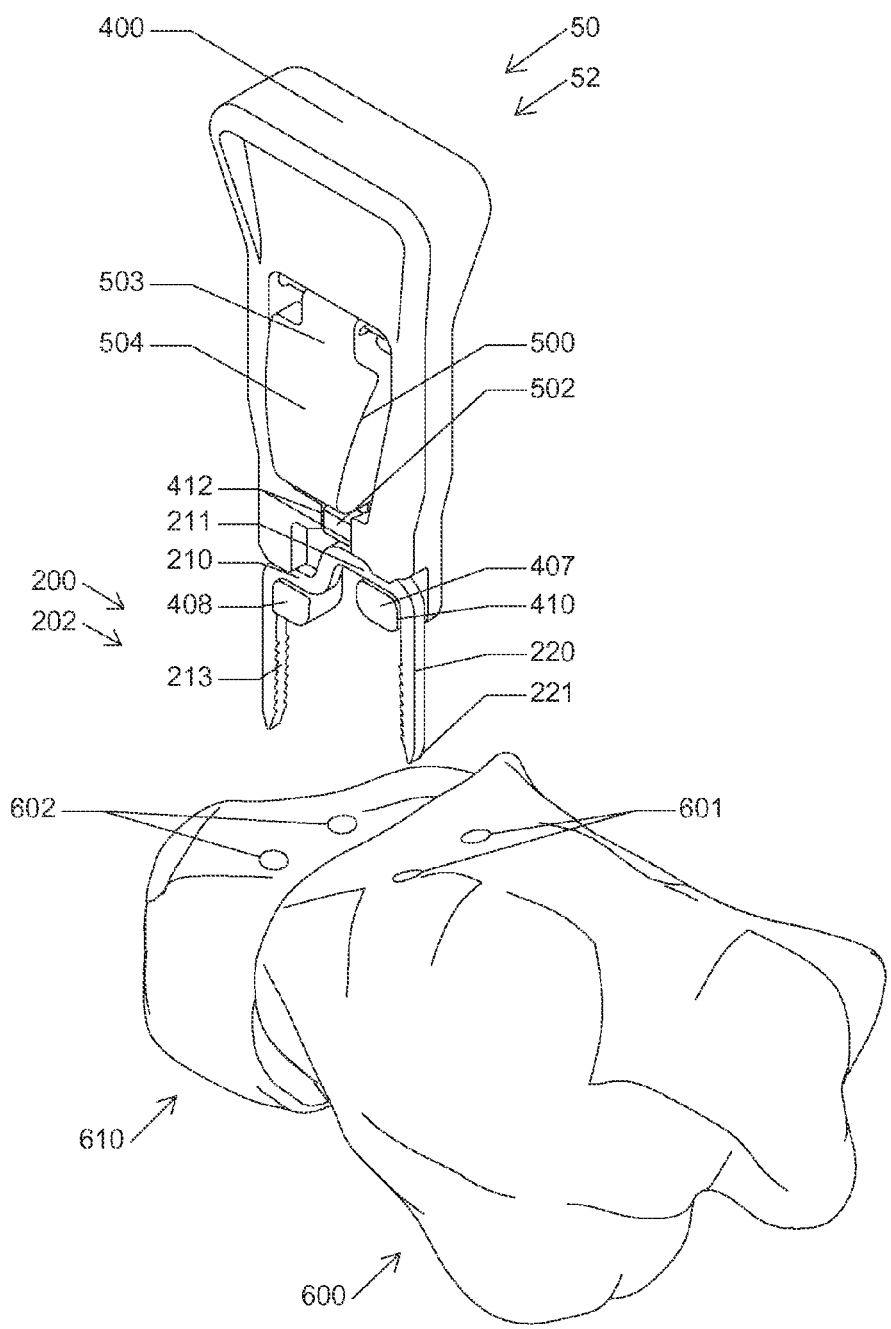
FIG. 32 is a perspective front view illustrating the implant insertion device in the engagement position with an implant loaded on the implant insertion device positioned for loading into bone.
Figure 33:
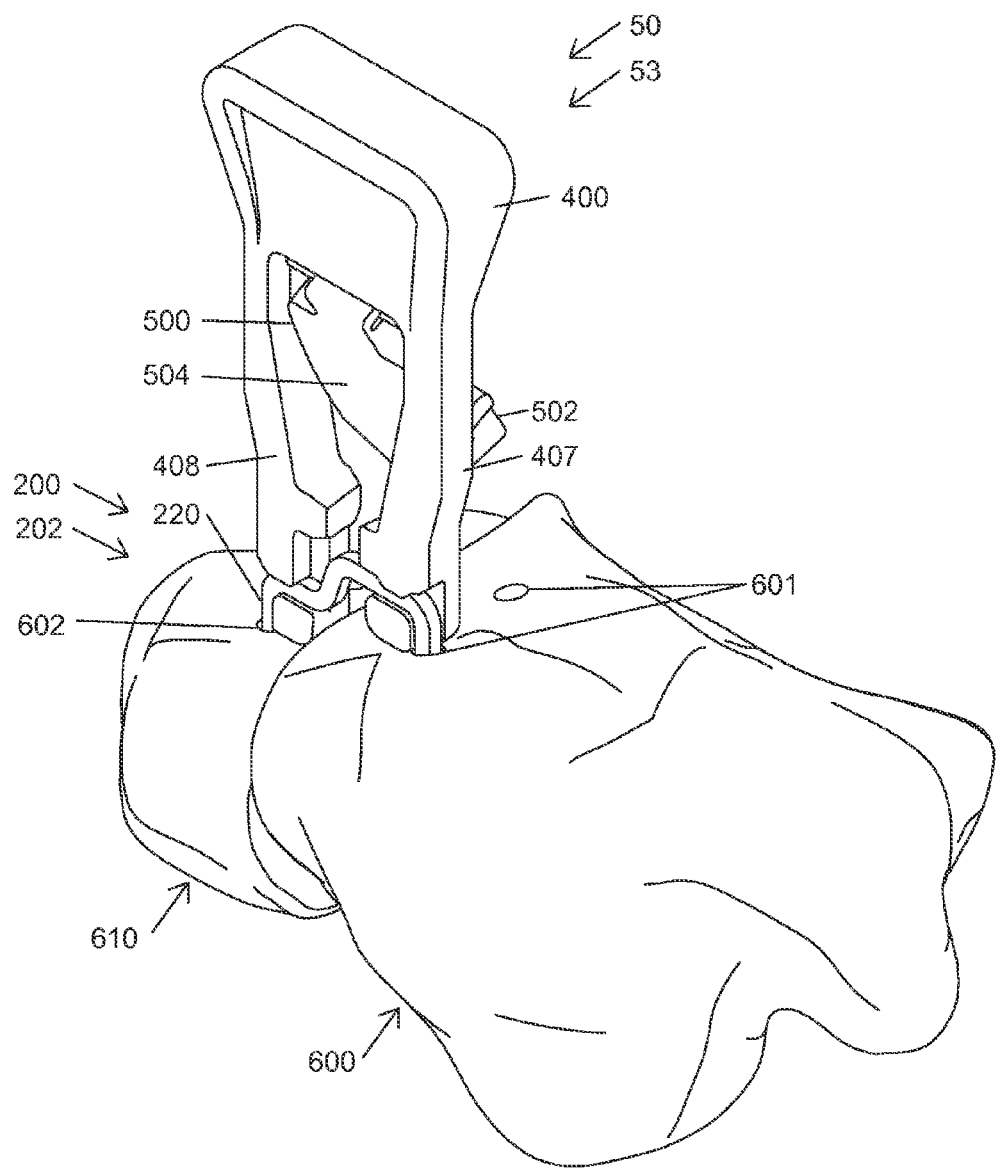
FIG. 33 is a perspective front view illustrating the implant insertion device in the disengagement position with the implant inserted into bone.
Figure 34:
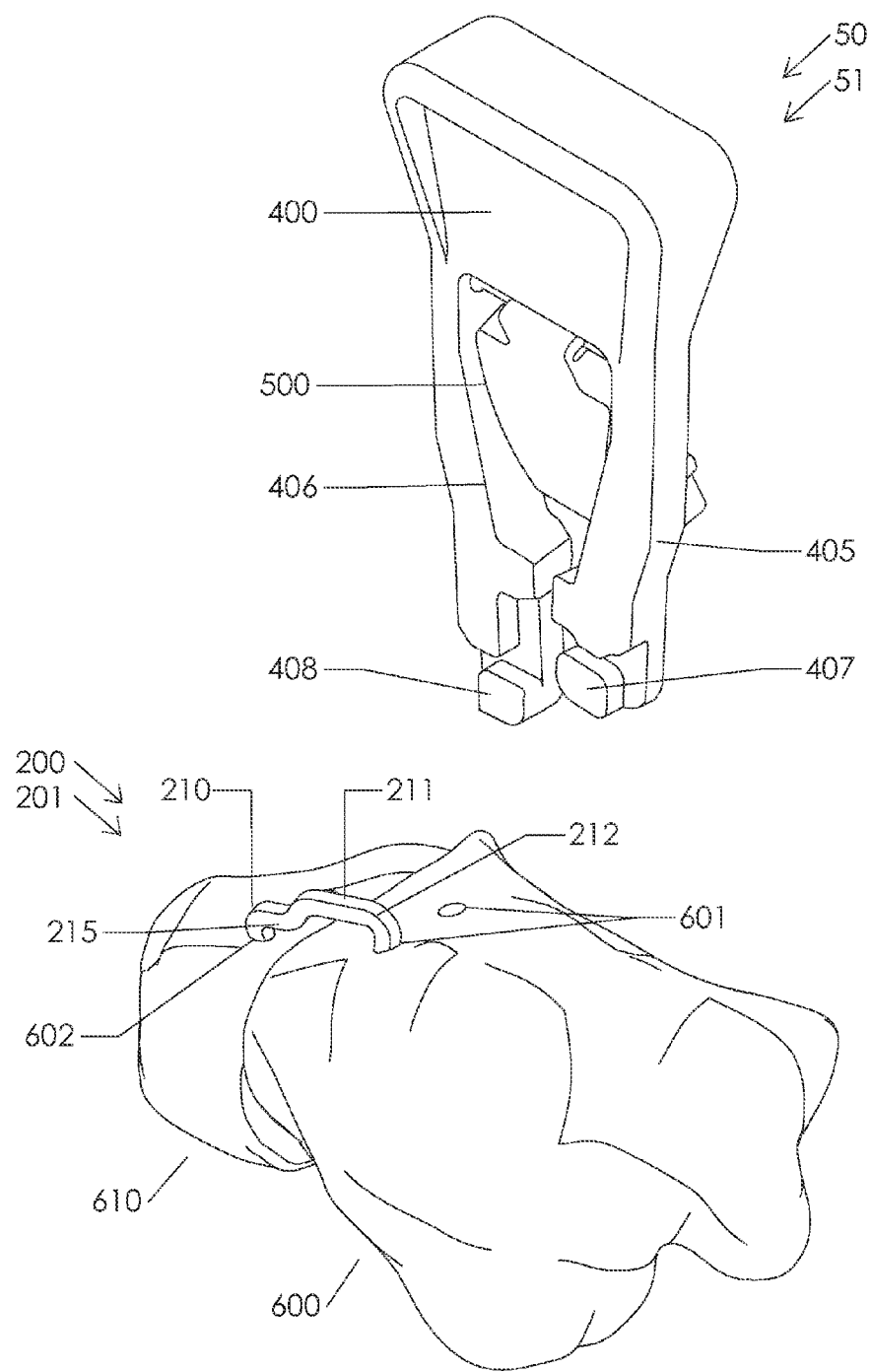
FIG. 34 is a perspective front view illustrating the implant insertion device in the disengagement position with the implant fully inserted into bone.

FIGS. 32-34 illustrate the operation of inserting the implant 200 into a first bone 600 and a second bone 610 using the implant insertion device 50 as well as the removal of the implant 200 from the implant insertion device 50. The implant 200 may be preloaded on the implant insertion device 50 prior to surgery or the implant 200 may be loaded on the implant insertion device 50 during surgery. The operation of the implant insertion device 50 is as follows.

In order to receive the implant 200, the spacer 500 of the implant insertion device 50 is moved to its unlocked position thereby placing the jaws 407 and 408 in the unengaged position. The implant 200 is then mechanically deformed from the first final shape 51 into the second shape 52 such that the implant 200 stores mechanical energy. After being mechanically deformed from the first final shape 51 into the second shape 52, the implant 200 is placed over the jaws 407 and 408 of the implant insertion device 50. The implant 200 is placed within the slots formed by the jaws 407 and 408. In particular, the implant 200 is placed over the jaws 407 and 408 such that at least a portion of the bottoms 213 of the bridges 210 and 211 resides adjacent the bridge interfaces 409, the back 214 resides adjacent an interior portion of the jaws 407 and 408, at least a portion of the tops 215 of the bridges 210 and 211 resides adjacent the stops 415 of the jaws 407 and 408, and the legs 220 reside adjacent the leg interfaces 410 of the jaws 407 and 408.

Figure 26:
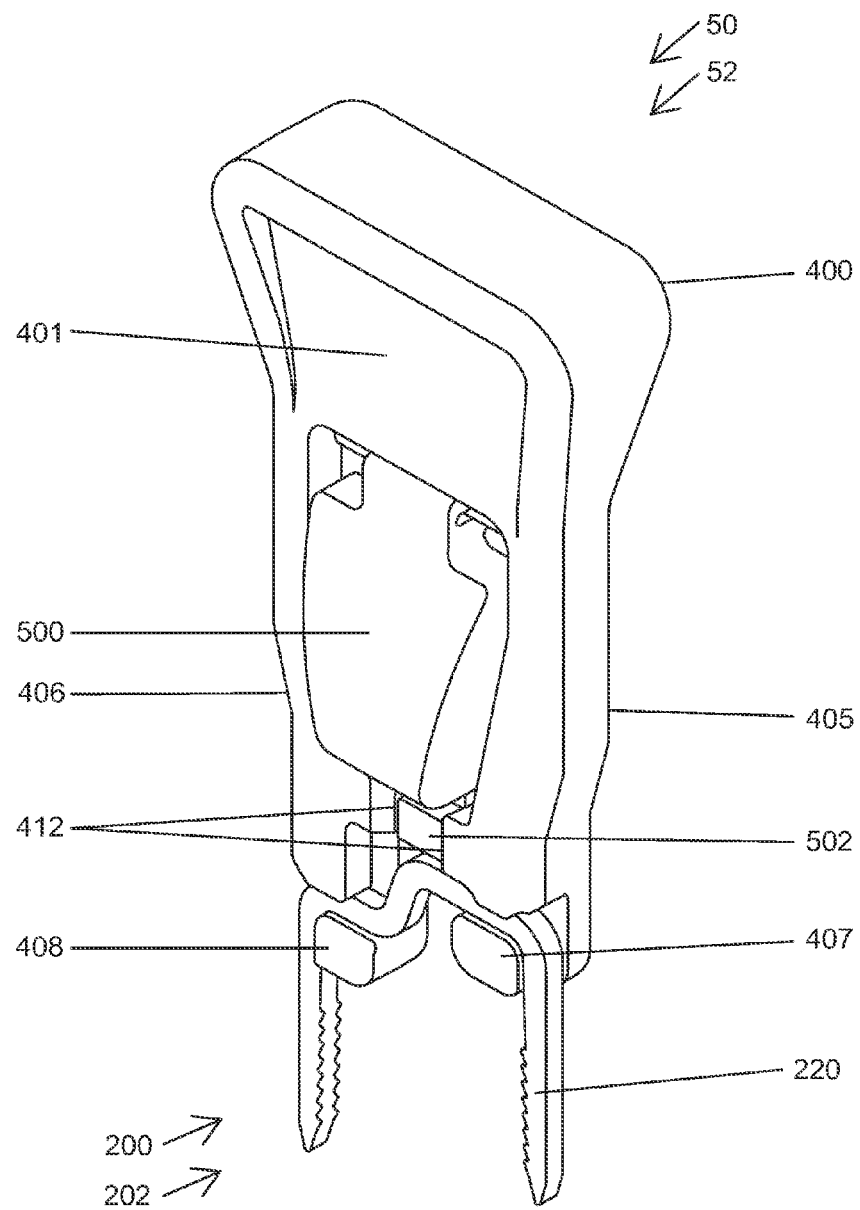
FIG. 26 is a perspective front view illustrating the implant insertion device in the implant engagement position with an implant loaded on the implant insertion device.
Figure 27:
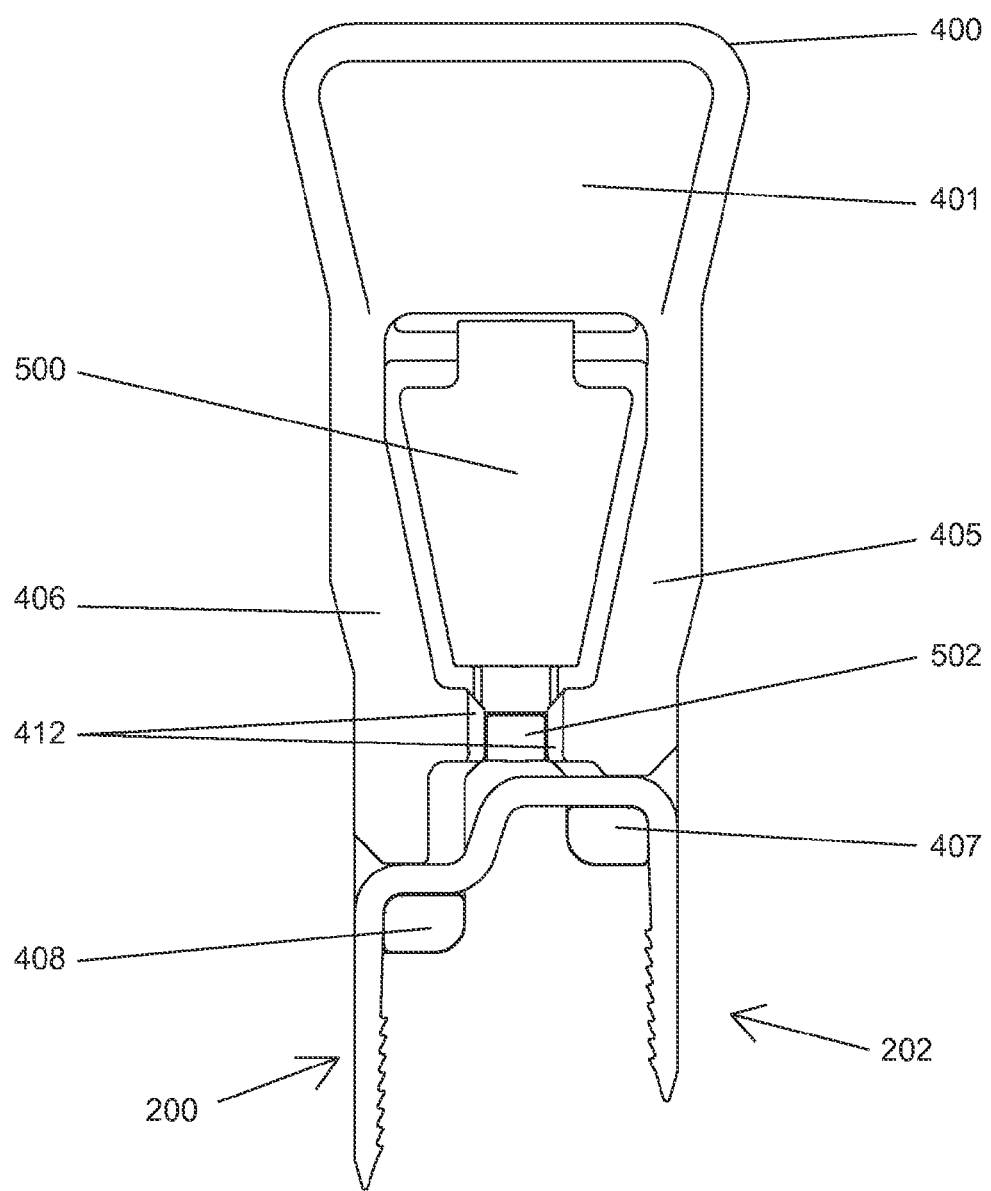
FIG. 27 is a front view of the implant insertion device in an engaged position loaded with the implant in a second shape.
Figure 28:
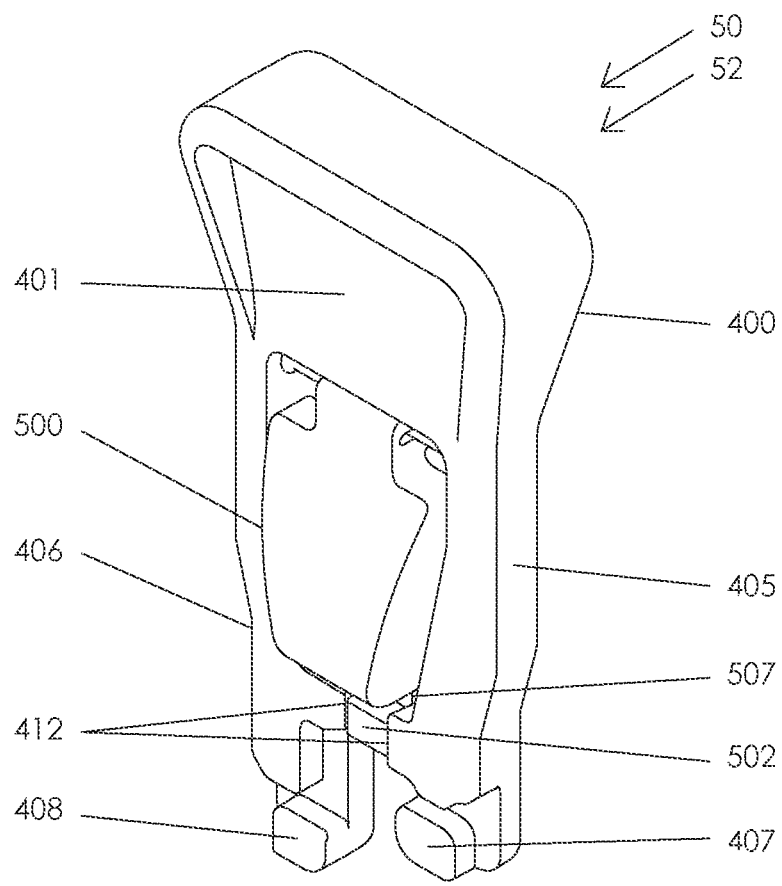
FIG. 28 is a perspective front view illustrating the implant insertion device in the implant engagement position.

After the implant 200 is placed over the jaws 407 and 408, the spacer 500 of the implant insertion device 50 is moved from its unlocked position into its locked position as illustrated in FIGS. 26 and 27. As the spacer 500 moves from its unlocked position to its locked position, the jaw interfaces 507 of the separator 502 abut the jaws 407 and 408 at the separator interfaces 412. The engagement of the separator 502 with the jaws 407 and 408 moves the leg interfaces 410 of the jaws 407 and 408 horizontally outward and upward in an arc towards the legs 220 of the implant 200. As illustrated in FIGS. 26 and 27, when the spacer 500 is in its locked position, the leg interfaces 410 of the jaws 407 and 408 will abut the legs 220 below the corners 411 of the implant 200, and the jaws 407 and 408 will be moved to their engaged position, thereby securing the implant 200 to the implant insertion device 50. In particular, the mechanical energy stored in the implant 200 tensions the implant 200 against the jaws 407 and 408 such that the implant 200 remains loaded on the implant insertion device 50 while the implant insertion device 50 also maintains the implant 200 in the second shape 202. In addition, the stops 415 provide a surface that aids in preventing the dislodgement of the implant 200 from the implant insertion device 50.

Figure 24:
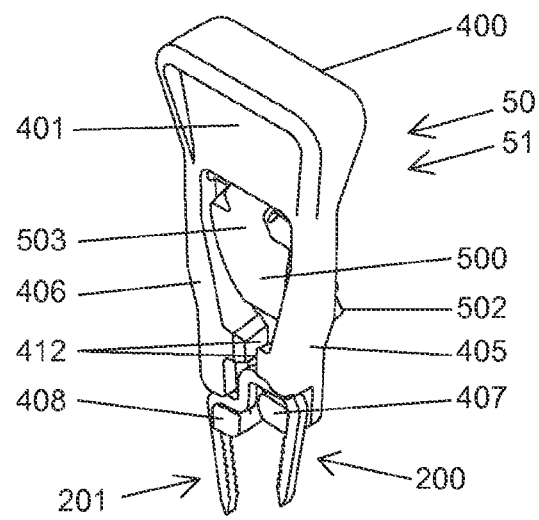
FIG. 24 is a perspective view of the implant insertion device in the disengaged position coupled with the implant in the first shape.
Figure 25:
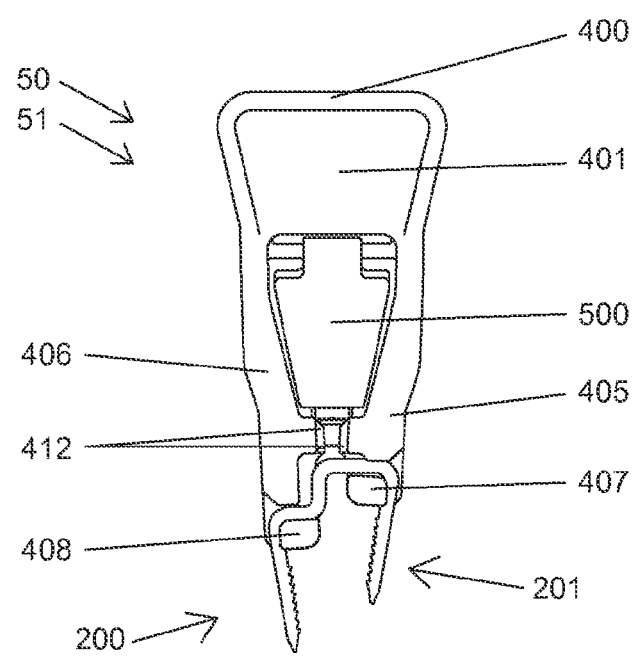
FIG. 25 is a front view of the implant insertion device in the disengaged position coupled with the implant in the first shape.

While the implant 200 may be mechanically deformed from the first final shape 201 into its second shape 202 before placement on the implant insertion device 50, the implant 200 more preferably is placed on the implant insertion device 50 in the first final shape 201 as illustrated by FIGS. 24 and 25 and then mechanically deformed to the second shape 202 by the implant insertion device 50 as illustrated by FIGS. 26 and 27. As the spacer 500 of the implant insertion device 50 is moved from its unlocked position to its locked position, the spacer 500 will engage the jaws 407 and 408, thereby moving the jaws 407 and 408 from their unengaged to their engaged position. The force of the spacer 500 moving the jaws 407 and 408 will be transferred to the implant 200 such that the implant 200 moves from its first final shape 201 to the second shape 202. This force transfer imparts mechanical energy into the implant 200 and tensions the implant 200 against the jaws 407 and 408 such that the implant 200 remains loaded on the implant insertion device 50 while the implant insertion device 50 also maintains the implant 200 in the second shape 202. Although not necessary, the implant 200 is preferably cooled prior to placement on the implant insertion device 50 in order to aid in movement of the implant 200 from its first final shape 201 to the second shape 202. Moreover, a mechanical press may be used to insert the spacer 500 between the jaws 407 and 408. Movement of an arm of the mechanical press places a press face against the spacer 500 and, ultimately, presses the spacer 500 between the jaws 407 and 408 such that the jaw interfaces 507 of the separator 502 abut the jaws 407 and 408 at the separator interfaces 412.

After the implant 200 is secured to the implant insertion device 50, the implant 200 is ready to be implanted into tissue or bones 600 and 610 as shown in FIG. 32. The surgeon places the tips 221 of the implant 200 into predrilled holes 601 and 602 or the tips may be impacted into the tissue or bones 600 and 610 thereby securing the implant 200 into the tissue or bones 600 and 610. Once the implant 200 is secured to the tissue or bones 600 and 610, it is ready for removal from the implant insertion device 50. To remove the implant 200 from the implant insertion device 20, the surgeon presses the actuator 503 at the front 504 of the spacer 500. Pressing the actuator 503 at the front 504 of the spacer 500 moves the spacer 500 from its locked position to its unlocked position as shown in FIG. 33. As the spacer 500 moves from its locked position to its unlocked position, the jaws interface 507 of the separator 502 disengages the jaws 407 and 408 at the separator interfaces 412. The disengagement of the separator 502 with the jaws 407 and 408 moves the jaws 407 and 408 from their engaged position to their unengaged position in that the leg interfaces 410 of the jaws 407 and 408 move horizontally inward and downward in an arc away from the legs 220 of the implant 200. Movement of the jaws 407 and 408 both horizontally inward and downward in an arc away from the legs 220 of the implant 200 enhances and simplifies separation of the implant insertion device 50 from the implant 200. When the spacer 500 is in its unlocked position and the jaws 407 and 408 are in their unengaged position, the leg interfaces 410 no longer abut the legs 220 of the implant 200, resulting in the release of the tension between the implant 200 and the jaws 407 and 408. The implant 200 accordingly no longer contacts and is no longer secured to the implant insertion device 50, thus allowing the removal of the implant 200 from the implant insertion device 50 as shown in FIG. 34.

In addition to the above-described method of removing the implant 200 from the implant insertion device 50, the implant 200 may be removed from the implant insertion device 50 by applying a twisting force to the implant insertion device 50. Specifically, after the tips 221 of the legs 220 are inserted into the tissue or bones 600 and 610, as illustrated in FIG. 32, the surgeon applies a twisting or rotational force to the implant insertion device 50 relative to the implant 200. The twisting or rotational force overcomes the force the jaws 407 and 408 apply against the implant 200. As a result, the jaws 407 and 408 separate from the implant 200, thereby releasing the implant 200 from the implant insertion device 50. In particular, the leg interfaces 410 of the jaws 407 and 408 separate from the legs 220 of the implant 200 such that the implant insertion device 50 is removed from the implant 200.

Removing the implant 200 from the implant insertion device 50 using a twisting or rotational force is possible due to the minimized contact between the implant 200 and the implant insertion device 50 when the implant 200 is secured to the implant insertion device 50. As described above, when the implant 200 is secured to the implant insertion device 50, the main contact point between the implant insertion device 50 and the implant 200 exists at the leg interfaces 410 of the jaws 407 and 408 and the legs 220. As such, only the force the jaws 407 and 408 apply against the implant 200 must be overcome in order for the implant 200 to be released from the implant insertion device 50. This minimizes the twisting or rotational force required for the release of the implant 200, thereby simplifying the removal of the implant 200 from the implant insertion device 50.

After the implant 200 is removed from the implant insertion device 50, as illustrated in FIG. 34, the implant 200 is tamped down to fully engage the tissue or bones 600 and 610. Once fully engaged, the implant 200 moves from its second shape 202 to its first final shape 201, thereby releasing its mechanical energy into the tissue or bones 600 and 610. As the implant 200 moves from its second shape 202 to its first final shape 201, the implant 200 places a constant force on the tissue or bone that fuses the tissue or bones 600 and 610 together and aids the healing process.

A method of loading the implant insertion device 10 with the implant 100 or the implant insertion device 50 with the implant 200 according to the preferred embodiment employs the temperature dependent shape memory properties of the implant 100 or 200. Specifically, upon application of a deformation temperature typically below the transformation temperature, the implant 100 can be mechanically deformed from its first final shape 101 into its second shape 102. After being mechanically deformed into the second shape 102, the implant 100 is held in the second shape 102 by the implant insertion device 10. Likewise, upon application of a deformation temperature typically below the transformation temperature, the implant 200 can be mechanically deformed from its first final shape 201 into its second shape 202. After being mechanically deformed into the second shape 202, the implant 200 is held in the second shape 202 by the implant insertion device 50.

FIGS. 35-41 illustrate a method of loading the implant insertion device 10 with the implant 100 according to a preferred embodiment. The method includes using a cryo-freezer 750, a cold table 751, and a press tool 259 to couple the implant 100 with the implant insertion device 10. Each method step of the preferred embodiment at any given time normally involves multiple implants 100 and multiple insertion devices 10, however, for the sake of disclosure and in order to aid in the understanding of the present invention, the method described herein will include only one implant 100 and one implant insertion device 10.

The implant insertion device 10 is placed into its implant disengagement position 11 in order to receive the implant 100. To place implant insertion device 10 into its disengagement position 11, the actuator 32 of the implant insertion device 10 is moved to its unlocked position thereby placing the jaws 40 in their disengaged position. The implant 100, which is in its first final shape 101, is placed over the 40. In particular, the implant 10 is placed over the jaws 40 such that the bottom 122 of the bridge 120 resides atop the bridge interfaces 42 of the jaws 40 and the legs 130 abut the leg interfaces 46 of the jaws 40. While the jaws 40 engage the implant 10 when in its first final shape 101 with sufficient force to maintain the implant 100 on the implant insertion device 10, the implant 100 is not sufficiently secured with the implant insertion device 10 to permit use during a surgery. Once the implant insertion device 10 engages the implant 100, the implant 100 and implant insertion device 10 are ready to be placed within the cryo-freezer 750.

Figure 35:
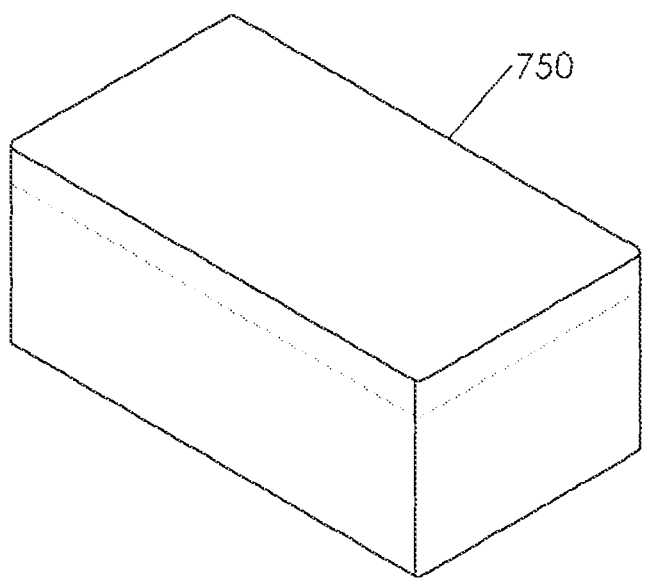
FIG. 35 is a perspective view of a cryo-freezer.
Figure 36:
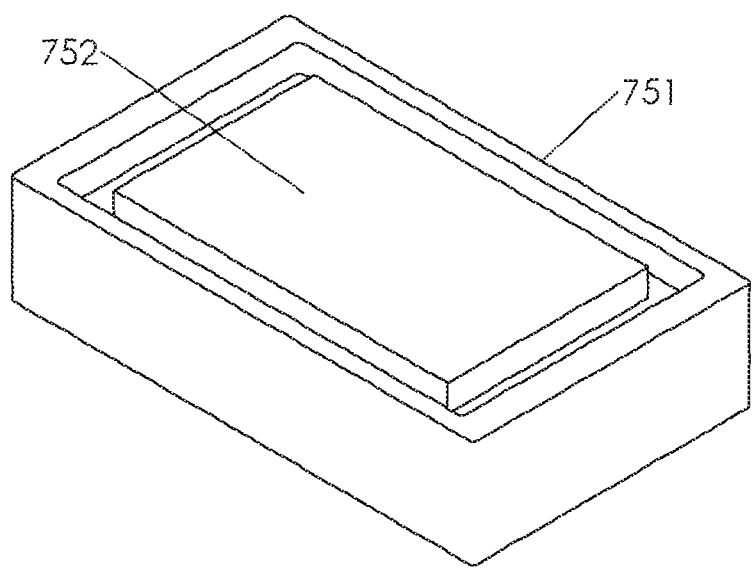
FIG. 36 is a perspective view of a cold table.

FIGS. 35 and 36 illustrate the cryo-freezer 750 and the cold table 751 which includes a platform 752. The implant 100 and the implant insertion device 10 are placed within the cryo-freezer 750 where the implant 100 experiences a reduction in temperature to a deformation temperature below its transition temperature and placing it in a malleable state. Once the implant 100 is at or below its deformation temperature, the implant 100 and the implant insertion device 10 are removed from the cryo-freezer 750 and placed on the platform 752 of the cold table 751. The cold table 751 aids in preventing the implant 100 from reaching its transition temperature after removal from the cryo-freezer 750. This is important when multiple implants 100 and implant insertion devices 10 are removed from the cryo-freezer 750 as it increases the time the implants 100 remain at their deformation temperature. In addition, the platform 752 allows the arranging of the implants 100 and the implant insertion devices 10 prior to the loading of the implant insertion devices 10 with implants 100 using the press tool 259. While the preferred embodiment places the implant 100 on the implant insertion device 10 prior to placement in the cryo-freezer 750, one of ordinary skill in the art will recognize that the implant 100 may be placed on the implant insertion device 10 after removal from the cryo-freezer 750.

Figure 37:
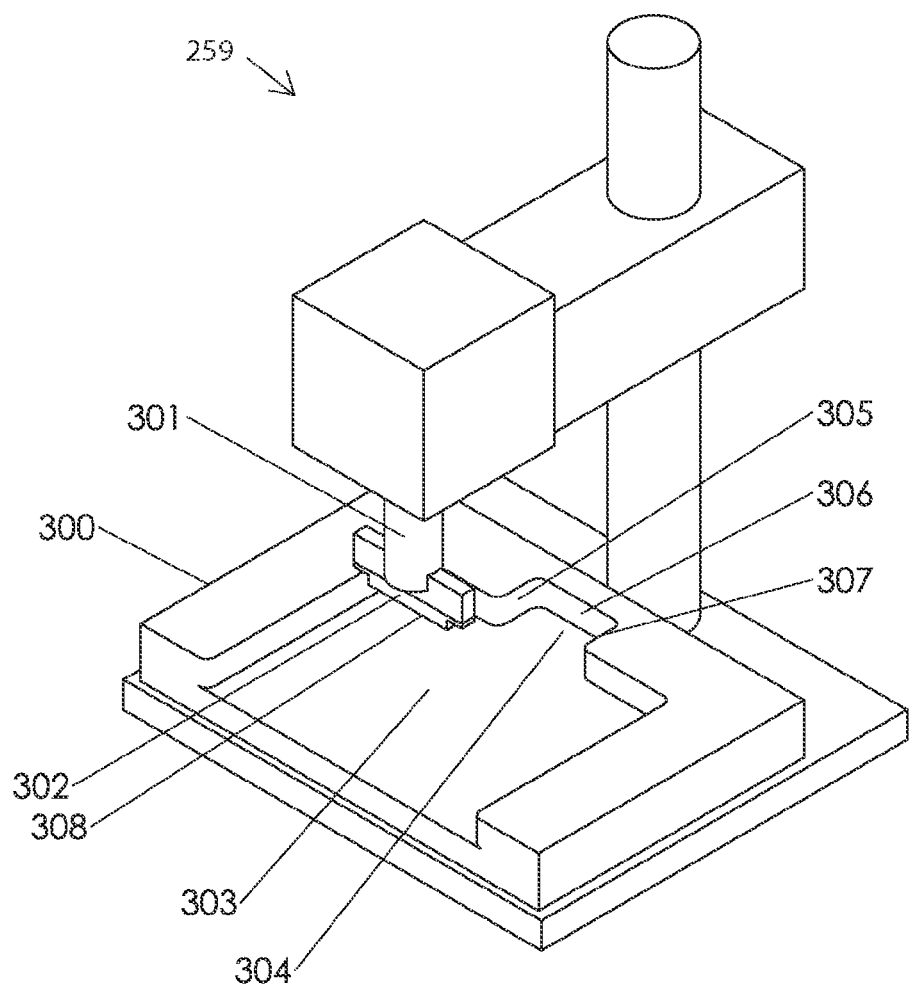
FIG. 37 is a perspective view of a press tool.

FIG. 37 illustrates a press tool 259 that includes an implant press base 300, a shaft 301, and a bumper 302 with a compression face 308. The implant press base 300 defines a loading surface 303 and a retainer 304. In the preferred embodiment, the retainer 304 includes three retention faces 305-307; nevertheless, one of ordinary skill in the art will recognize that the retainer may comprise a collar or any other device suitable to hold the implant insertion device 10. The bumper 302 may be composed of different materials to achieve varying results, however, in the preferred embodiment the bumper is composed of nylon. In addition, the press tool 259 in the preferred embodiment is a pneumatic press; however, one of ordinary skill in the art will recognize that any form of press tool may be implemented.

Figure 38:
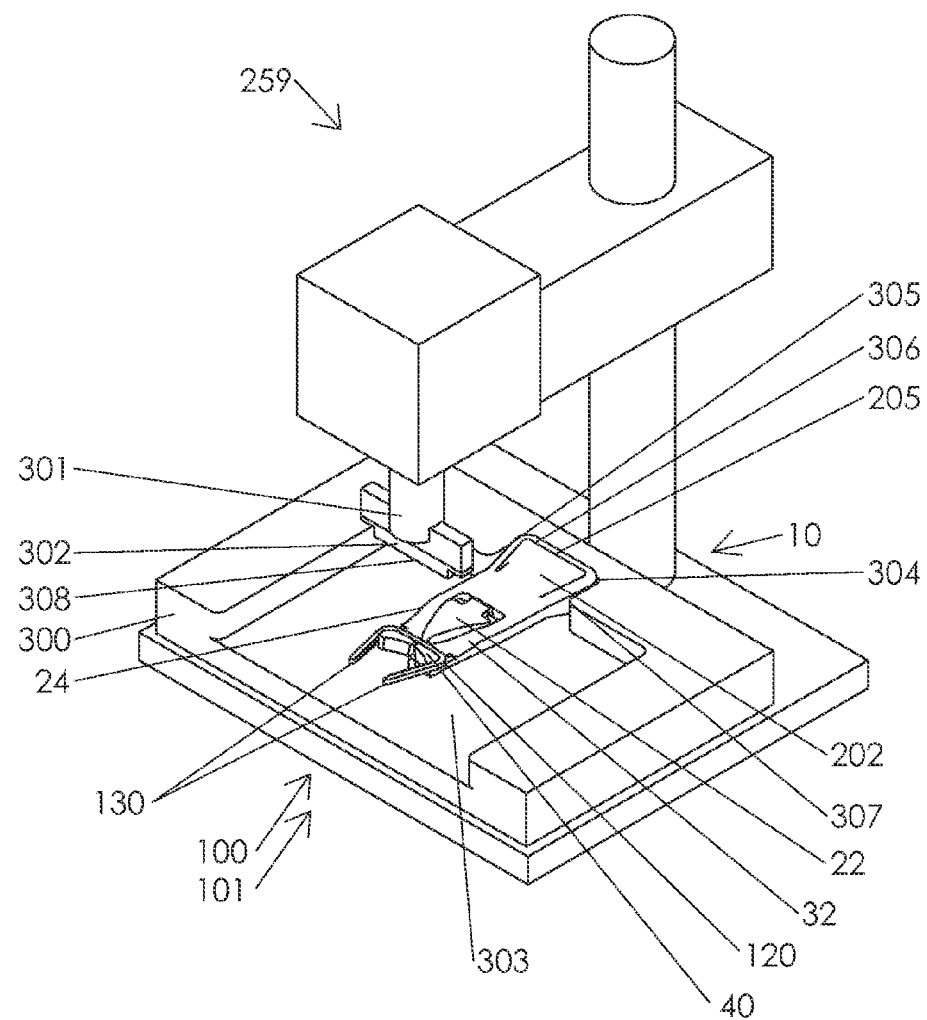
FIG. 38 is a perspective view of the press tool with the implant insertion device in the disengaged position and coupled with the implant in the first shape.

As illustrated in FIG. 38, the implant insertion device 10 with the implant 100 is placed upon the implant press base 300 of the press tool 259 such that the back 16 of the implant insertion device 10 is flush with the loading surface 303 and the retainer 304 of the implant press base 300. Furthermore, the handle 18 of the implant insertion device 10 fits within the retainer 304. In particular, the handle 18 is set between the retention face 305 and the retention face 307 with the top 15 of the handle 18 set flush against the retention face 306. Placing the handle 18 within the retainer 304 secures the implant insertion device 10 to the press tool 259. Once the press tool 259 retains the implant insertion device 10 with the implant 100, the press tool 259 is ready to fully secure and thus load the implant insertion device 10 with the implant 100.

Figure 39:
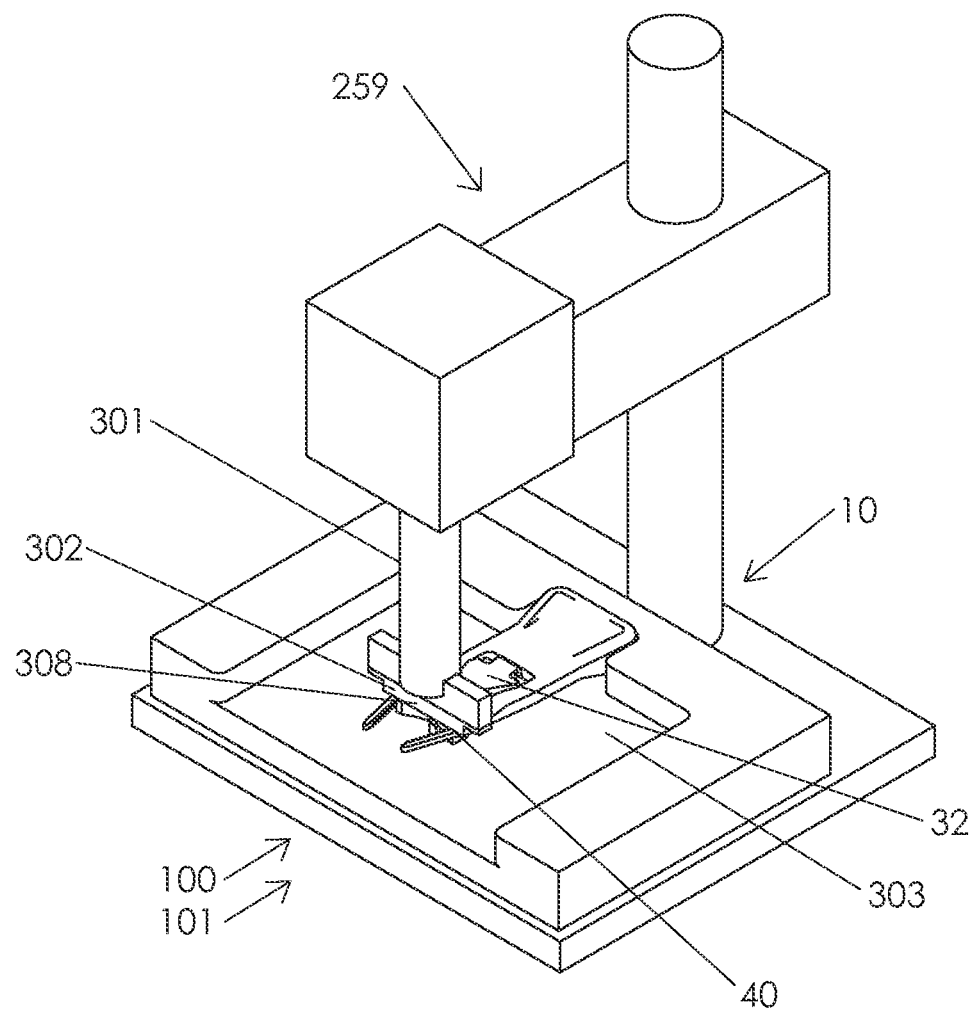
FIG. 39 is a perspective view of the press tool operating on the implant insertion device when in the disengaged position and coupled with the implant in the first shape.

As illustrated in FIG. 39, actuation of the press tool 259 operates the shaft 301 such that the shaft 301 moves to contact the compression face 308 of the bumper 302 with the jaws 40 of the implant insertion device 10 and the front 124 of the bridge 120 for the implant 100. After contacting the jaws 40 and the front 124 of the bridge 120, the press tool 259 applies a predetermined load at a predetermined speed onto the jaws 40 and the front 124 of the bridge 120 through the compression face 308 of the bumper 302.

Once the compression face 302 applies the predetermined load onto the jaws 40 and the front 124 of the bridge 120, the actuator 32 moves from its unlocked position to its locked position. As the actuator 32 moves from its unlocked position to its locked position, the separator 35 inserts between the arms 22 and 24 and the jaws 40. After the actuator 32 moves to its locked position, the separator 35 resides between and abuts the arms 22 and 24 and the jaws 40 such that the jaws interface 36 of the separator 35 abuts the separator interfaces 48 of the jaws 40.

When not abutted by the separator 35, the arms 22 and 24 maintain the jaws 40 canted downward, however, inserting the separator 35 between the arms 22 and 24 and the jaws 40 spreads the arms 22 and 24 and the jaws 40. In particular, the separator 35 moves the arms 22 and 24 and the jaws 40 horizontally outward and in an upward arc such that the jaws 40 travel from their disengaged position to their engaged position. After the jaws 40 reach their engaged position the leg interfaces 46 of the jaws 40 will abut the legs 130 of the implant 100.

Figure 40:
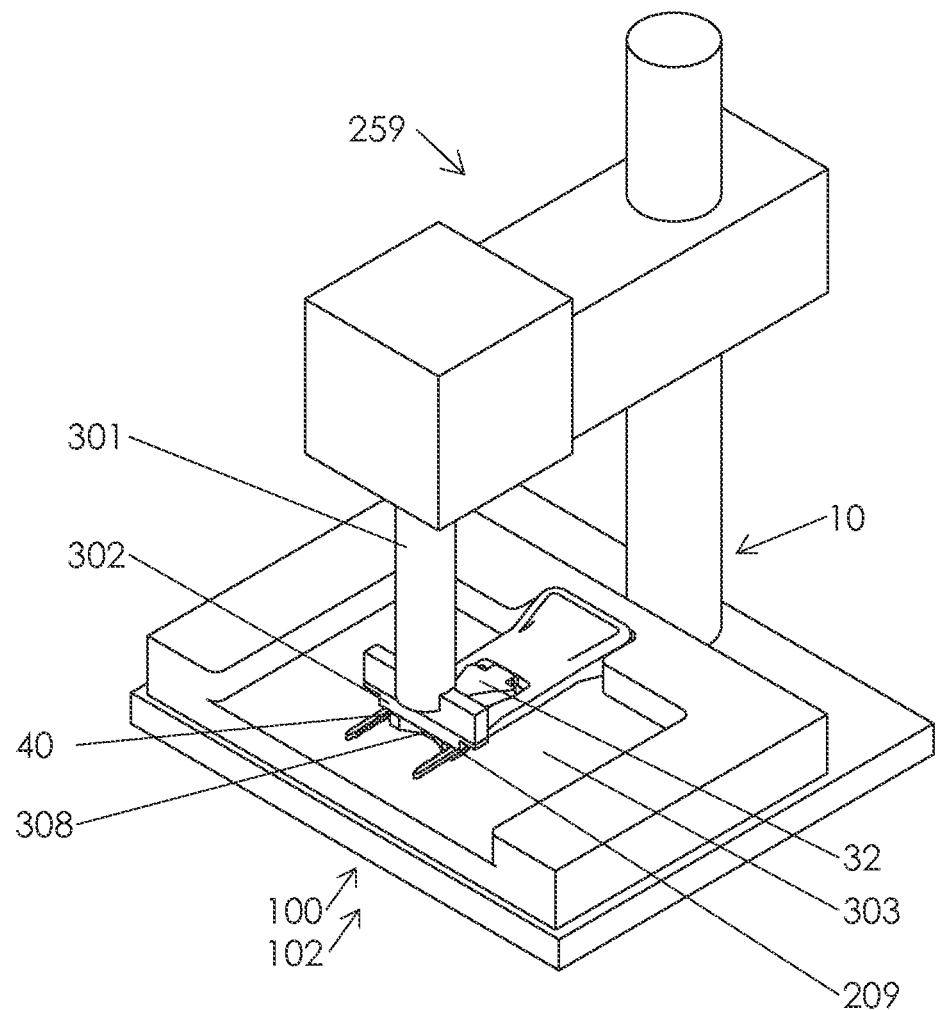
FIG. 40 is a perspective view of the press tool operating on the implant insertion device such that the implant insertion device is in the engaged position and loaded with the implant in the second shape.

As illustrated in FIG. 40, the movement of the jaws 40 from their disengaged position to their engaged position as well as the application to the bridge 120 of the predetermined load by the compression face 302 mechanically deforms the implant 100 from its first final shape 101 into its second shape 102 thereby loading the implant insertion device 10 with the implant 100. By mechanically deforming the implant 100, the implant 100 stores mechanical energy within the implant 100. In particular, the mechanical energy stored within the implant 100 tensions the implant 100 against the jaws 40 such that the implant insertion device 10 remains loaded with the implant 100 while the implant insertion device 10 also maintains the implant 100 in the second shape 102.

Figure 41:
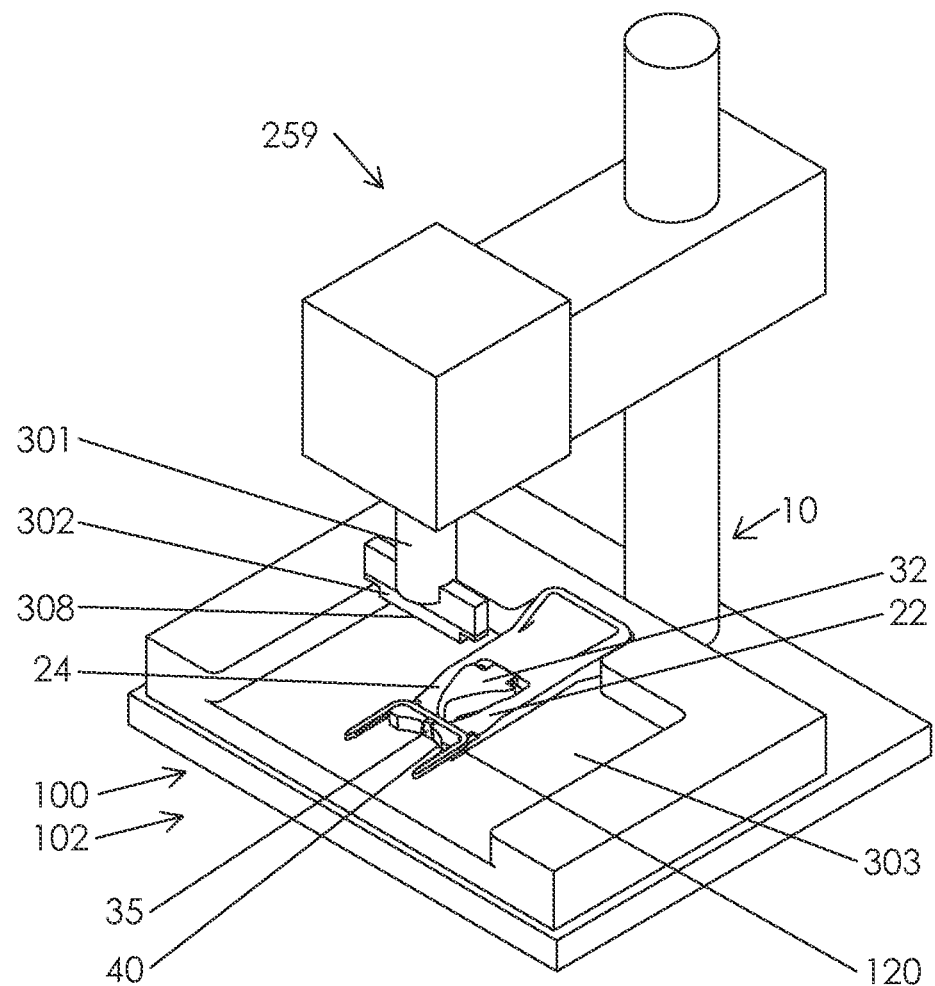
FIG. 41 is a perspective view of the press tool with the implant insertion device in the engaged position and loaded with the implant in the second shape.

As illustrated in FIG. 41, after loading the implant insertion device 10 with the implant 100, the shaft 301 of the press tool 259 is retracted so that the compression face 308 of the bumper 302 is removed from the jaws 40 of the implant insertion device 10 and the bridge 120 of implant 100. Following the retraction of the shaft 301, the implant insertion device 10 loaded with the implant 100 is ready for shipment or implantation into tissue or bone. In the case of shipment, the implant insertion device 10 loaded with the implant 100 is packaged in a container designed to hold the implant insertion device 10 loaded with the implant 100. It should be understood that the pre-loading and packaging of the implant insertion device 10 with the implant 100 allows for sterilizing of the implant insertion device 10 and the implant 100 by any common sterilization method such as gas, radiation, or another type as well as delivery of the implant insertion device 10 and the implant 100 in sterile condition.

While the method of loading an implant insertion device with an implant has been described using the implant insertion device 10 and the implant 100, one of ordinary skill in the art will recognize that the method is identical for loading an implant insertion device 50 with an implant 200. However, it should be understood that, in the step of loading the implant insertion device 50 with implant 200 using the press tool 259, the compression face 308 of the bumper 302 contacts the jaws 407 and 408 of the implant insertion device 50 and the fronts 215 of the bridges 210 and 211 for implant 200.

The preferred method reduces the temperature of the implant 10 or 200 to a deformation temperature on the basis the shape memory properties of an implant at a deformation temperature allow efficient manipulation of the implant from its first final shape to its second shape. Nevertheless, one of ordinary skill in the art will recognize that a press tool 259 applying appropriate force with a compression face 308 that ensures an implant 10 or 200 remains contacted with an implant insertion device 10 or 50 during force application may be used to load an implant insertion device 10 or 50 with an implant 100 or 200.

Figure 42:
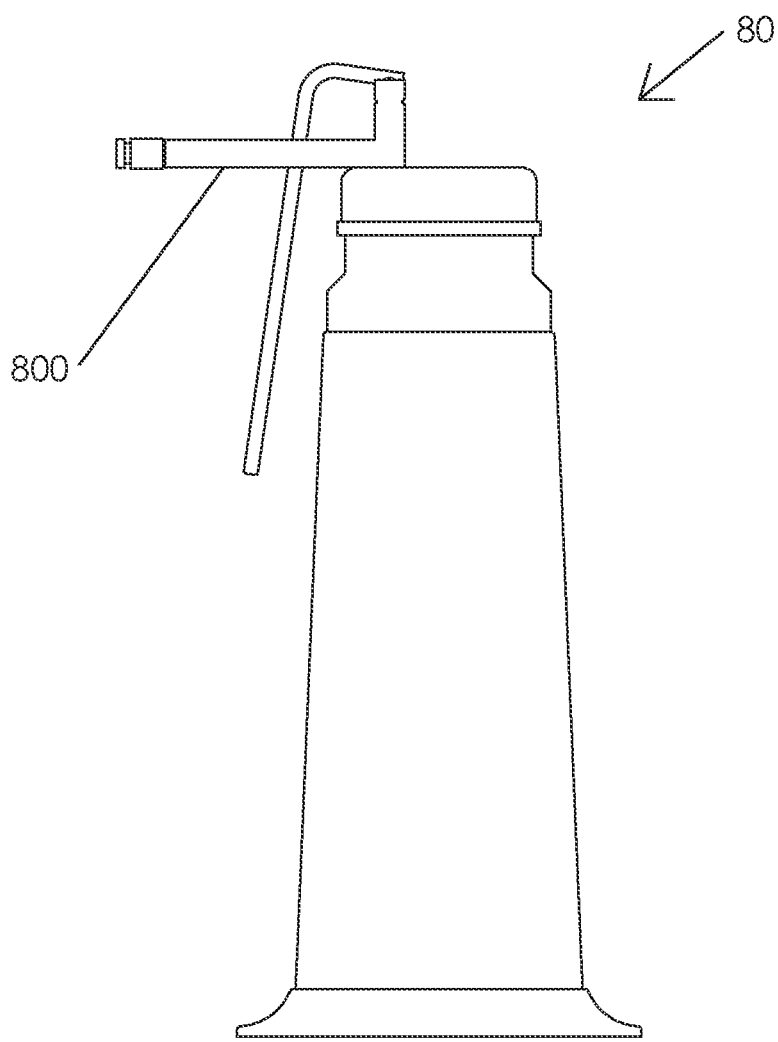
FIG. 42 is a side view of a liquid nitrogen spray canister.
Figure 43:
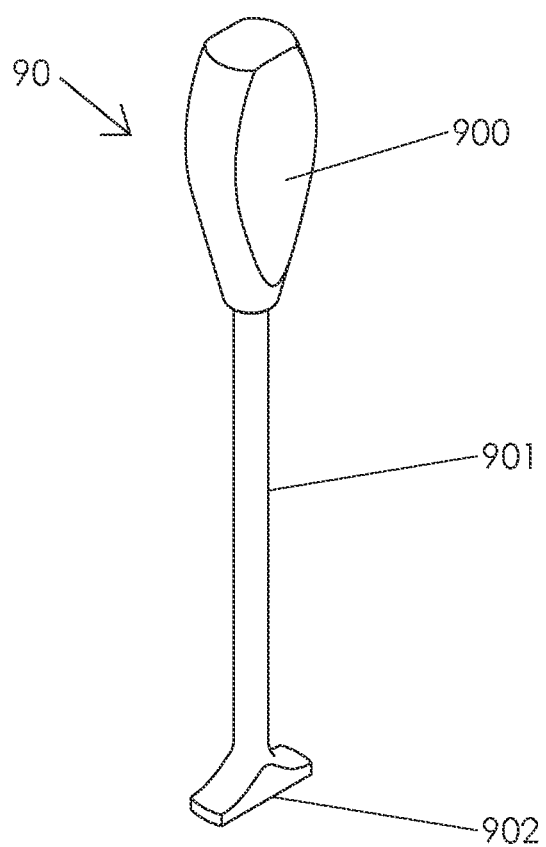
FIG. 43 is a perspective view of a tamp.

FIGS. 42-47 illustrate an alternative embodiment for the method of loading the implant insertion device 10 with the implant 100. The alternative embodiment for the method allows the loading of the implant insertion device 10 with the implant 100 in the event the implant insertion device 10 was not pre-loaded and must be loaded in the field prior to a surgery, or even for demonstration purposes. FIG. 42 illustrates a liquid nitrogen spray canister 80 that includes a nozzle 800. FIG. 43 illustrates a press tool, which in the alternative embodiment is a tamp 90 that includes a handle 900, a load member 901, and a compression face 902. The alternative method includes using the liquid nitrogen spray canister 80 and the tamp 90 to load the implant insertion device 10 with the implant 100.

The implant insertion device 10 is placed into its implant disengagement position 11 in order to receive the implant 100. To place implant insertion device 10 into its disengagement position 11, the actuator 32 of the implant insertion device 10 is moved to its unlocked position thereby placing the jaws 40 in their disengaged position. The implant 100, which is in its first final shape 101, is placed over the jaws 40. In particular, the implant 100 is placed over the jaws 40 such that the bottom 122 of the bridge 120 resides atop the bridge interfaces 42 of the jaws 40 and the legs 130 abut the leg interfaces 46 of the jaws 40. While the jaws 40 engage the implant 100 when in its first final shape 101 with sufficient force to maintain the implant 100 on the implant insertion device 10, the implant 100 is not sufficiently secured with the implant insertion device 10 to permit use during a surgery. Once the implant insertion device 10 engages the implant 100, the implant 100 and implant insertion device 10 are ready for the liquid nitrogen spray canister 80 to deliver liquid nitrogen to the implant 100.

Figure 44:
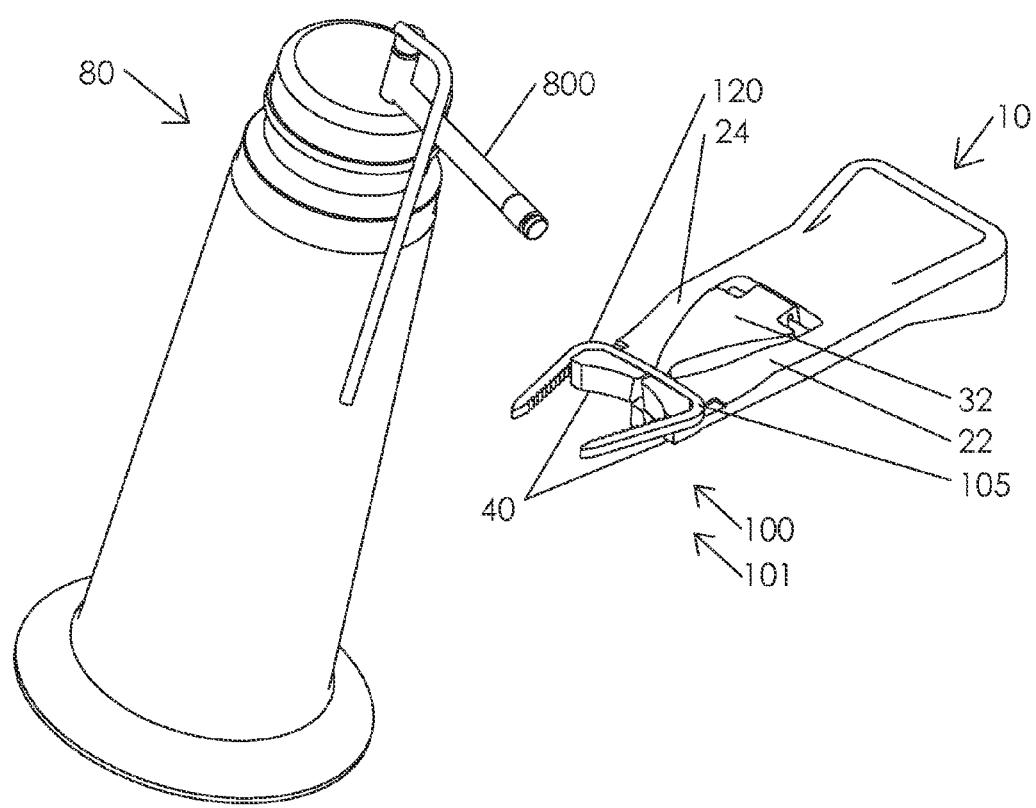
FIG. 44 is a perspective view of the liquid nitrogen spray canister delivering liquid nitrogen to the implant.

FIG. 44 illustrates the canister 80 delivering vaporized liquid nitrogen through the nozzle 800 onto the implant 100. The implant 100 experiences a reduction in temperature to a deformation temperature below its transition temperature. Once the implant 100 is at or below its deformation temperature, the implant 100 is ready to fully secure and thus load onto the implant insertion device 10 using the tamp 90. While the alternative embodiment for the loading method places the implant 100 on the implant insertion device 10 prior to the canister 80 delivering vaporized liquid nitrogen to the implant 100, one of ordinary skill in the art will recognize that the implant 100 may be placed on the implant insertion 10 device after the canister 80 delivers vaporized liquid nitrogen to the implant 100.

Figure 45:
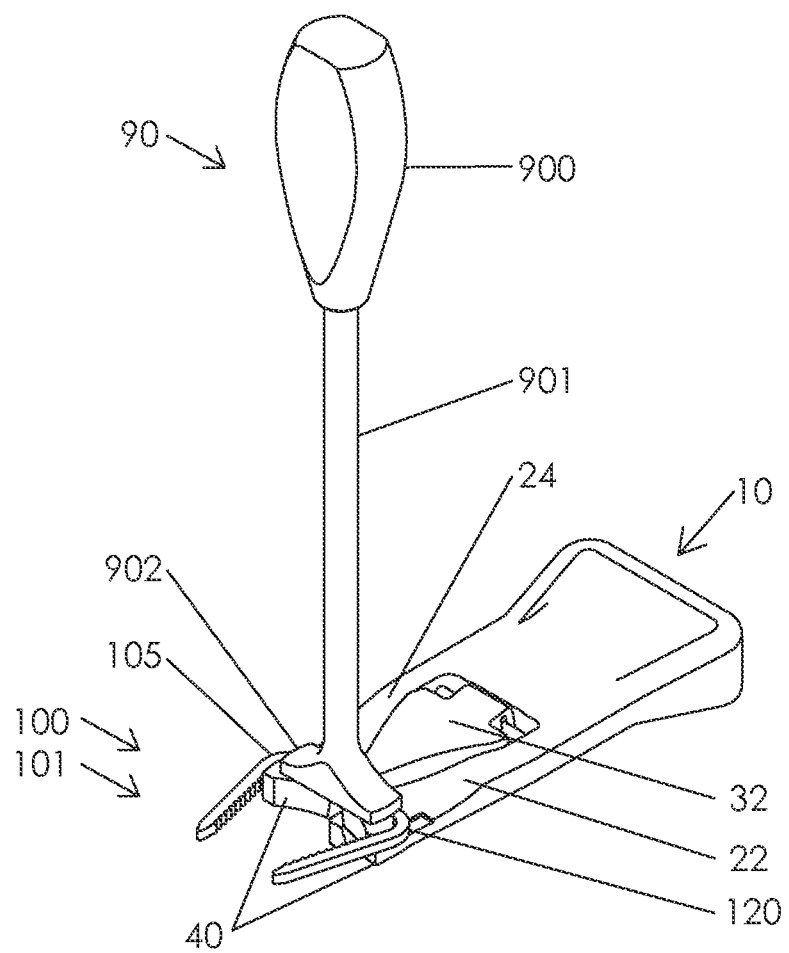
FIG. 45 is a perspective view of the tamp contacted with the implant insertion device in the disengaged position and coupled with the implant in the first shape.
Figure 46:
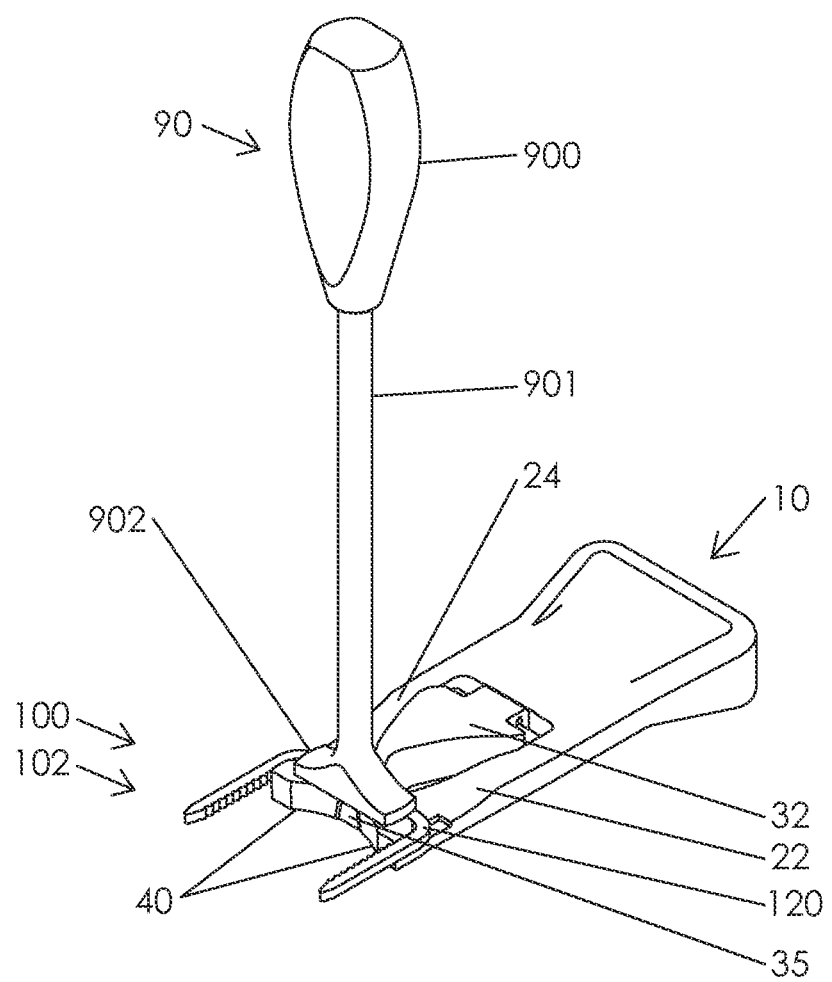
FIG. 46 is a perspective view of the tamp operating on the implant insertion device such that the implant insertion device is in the engaged position and loaded with the implant in the second shape.
Figure 47:
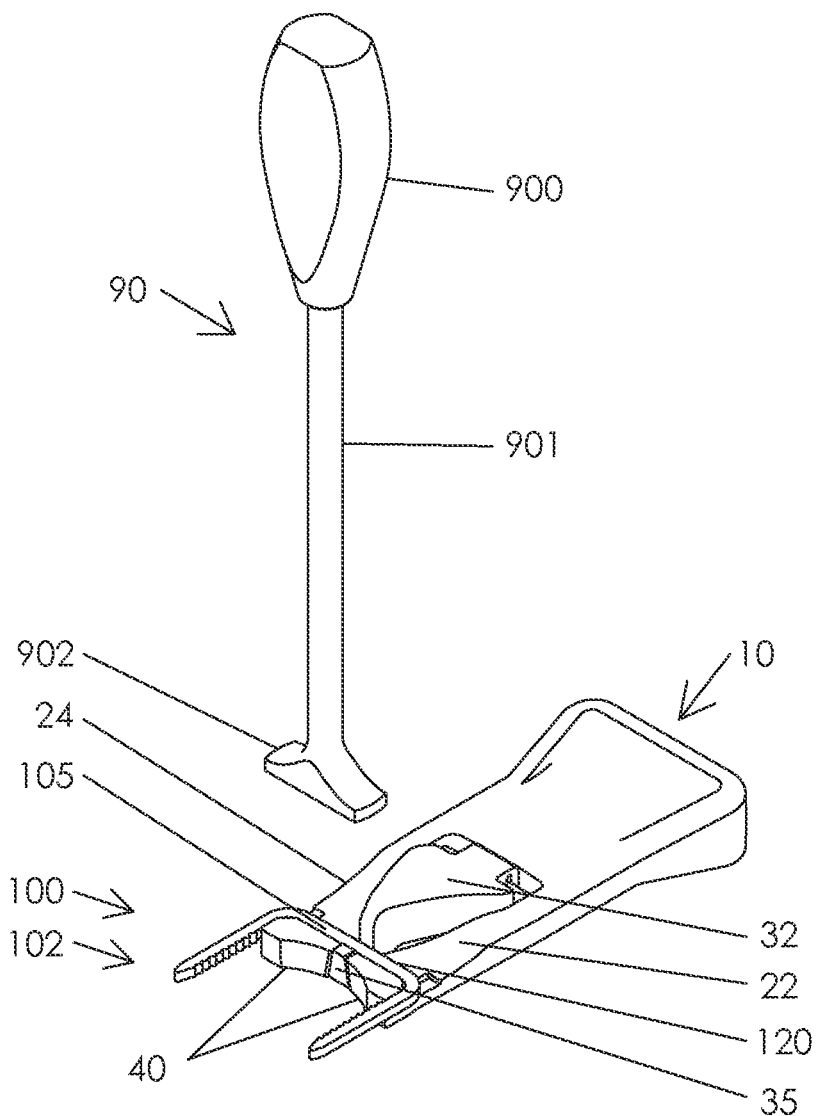
FIG. 47 is a perspective view of the tamp removed from the implant insertion device once the implant insertion device is in the engaged position and loaded with the implant in the second shape.

FIGS. 45-47 illustrate the tamp 90 loading the implant insertion device 10 with the implant 100. As illustrated in FIG. 45, a user employs the handle 900 to move the compression face 902 of the tamp 90 into contact with the jaws 40 of the implant insertion device 10 and the front 105 of the bridge 120 for the implant 10. After contacting the jaws 40 and the front 105 of the bridge 120, the user via the handle 900 and the load member 901 applies a load onto the jaws 40 and the front 105 of the bridge 120 through the compression face 902.

As illustrated in FIG. 46, the actuator 32 moves from its unlocked position to its locked position once the compression face 902 applies the load onto the jaws 40 and the front 105 of the bridge 120. As the actuator 32 moves from its unlocked position to its locked position, the separator 35 inserts between the arms 22 and 24 and the jaws 40. After the actuator 32 moves to its locked position, the separator 35 resides between and abuts the arms 22 and 24 and the jaws 40 such that the jaws interface 36 of the separator 35 abuts the separator interfaces 48 of the jaws 40.

When not abutted by the separator 35, the arms 22 and 24 maintain the jaws 40 canted downward, however, inserting the separator 35 between the arms 22 and 24 and the jaws 40 spreads the arms 22 and 24 and the jaws 40. In particular, the separator 35 moves the arms 22 and 24 and the jaws 40 horizontally outward and in an upward arc such that the jaws 40 travel from their disengaged position to their engaged position. After the jaws 40 reach their engaged position the leg interfaces 46 of the jaws 40 will abut the legs 130 of the implant 100.

The movement of the jaws 40 from their disengaged position to their engaged position as well as the application of a load to the bridge 120 by the compression face 902 mechanically deforms the implant 100 from its first final shape 101 into its second shape 102, thereby loading the implant insertion device 10 with the implant 100. By mechanically deforming the implant 100, the implant 100 stores mechanical energy therein. In particular, the mechanical energy stored within the implant 100 tensions the implant 100 against the jaws 40 such that the implant insertion device 10 remains loaded with the implant 100 while the implant insertion device 10 also maintains the implant 100 in the second shape 102.

As illustrated in FIG. 47, the tamp 90 is removed after the implant insertion device 10 is loaded with the implant 100. In particular, the compression face 902 no longer contacts the jaws 209 of the implant insertion device 20 and the bridge 120 of implant 100. Following the removal of the tamp 90, the implant insertion device 10 loaded with the implant 100 is ready implantation into tissue or bone. One of ordinary skill in the art will recognize that there are many mechanisms other than a tamp that can be used for the loading method.

While the method of loading an implant insertion device with an implant according to the alternative method has been described using the implant insertion device 10 and the implant 100, one of ordinary skill in the art will recognize that the method is identical for loading an implant insertion device 50 and an implant 200. However, it should be understood that, in the step of loading the implant insertion device 50 with implant 200 using the tamp 90, the compression face 902 contacts the jaws 407 and 408 of the implant insertion device 50 and the fronts 215 of the bridges 210 and 211 for implant 200.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An implant insertion device adapted to move a shape memory implant from a first shape to a second shape and maintain the shape memory implant in the second shape until the delivery of the shape memory implant into tissue or bone, comprising:
   (i) a body, comprising:
      a first arm including a first jaw adapted to engage the shape memory implant, and
      a second arm including a second jaw adapted to engage the shape memory implant, wherein the first jaw and the second jaw are movable from a disengaged position to an engaged position; and
   (ii) a spacer coupled with the body and movable between an unlocked position and a locked position, wherein the spacer in its locked position inserts between the first jaw and the second jaw and urges the first and second jaws to their engaged positions such that the first and second jaws engage the shape memory implant and move the shape memory implant from its first shape to its second shape, further wherein the first and second jaws in their engaged positions maintain the shape memory implant in the second shape.

2. The implant insertion device according to claim 1, wherein the first jaw and second jaw experience a rotation relative to the first arm and second arm when the spacer is moved from its unlocked to its locked position.

3. The implant insertion device according to claim 1, wherein the implant insertion device is adapted to deliver the shape memory implant into tissue or bone.

4. The implant insertion device according to claim 3, wherein, after the implant insertion device delivers the shape memory implant into tissue or bone, movement of the spacer from its locked position to its unlocked position releases the spacer from between the first jaw and the second jaw, further wherein the first and second jaws move from their engaged positions to their disengaged positions such that the first and second jaws disengage from the shape memory implant, thereby releasing the shape memory implant and allowing the shape memory implant to move from its second shape to its first shape.

5. The implant insertion device of claim 4, wherein movement of the first and second jaws to the disengaged position further results in rotation of the first and second jaws away from the legs of the shape memory implant.

6. The implant insertion device according to claim 1, wherein:
   the first arm maintains the first jaw canted downward when the spacer resides in its unlocked position; and
   the second arm maintains the second jaw canted downward when the spacer resides in its unlocked position.

7. The implant insertion device according to claim 6, wherein insertion of the spacer between the first and second jaws to its locked position moves the first and second jaws horizontally outward and in an upward arc to their engaged positions such that the first and second jaws engage the shape memory implant and move the shape memory implant from its first shape to its second shape, further wherein the first and second jaws in their engaged positions maintain the shape memory implant in the second shape.

8. The implant insertion device according to claim 1, wherein:
the first jaw comprises a leg interface that abuts a first leg of the shape memory implant when the first jaw resides in its engaged position; and
the second jaw comprises a leg interface that abuts a second leg of the shape memory implant when the second jaw resides in its engaged position.

9. The implant insertion device according to claim 8, wherein:
the first jaw comprises a bridge interface, wherein, when the first jaw resides in its engaged position, at least a portion of a bridge of the shape memory implant resides atop the bridge interface; and
the second jaw comprises a bridge interface, wherein, when the second jaw resides in its engaged position, at least a portion of a bridge of the shape memory implant resides atop the bridge interface.

10. The implant insertion device according to claim 9, wherein:
the first jaw comprises a stop disposed above the bridge interface, the stop and the bridge interface defining a slot wherein, when the first jaw resides in its engaged position, at least a portion of a bridge of the shape memory implant resides in the slot; and
the second jaw comprises a stop disposed above the bridge interface, the stop and the bridge interface defining a slot wherein, when the second jaw resides in its engaged position, at least a portion of a bridge of the shape memory implant resides in the slot.

11. The implant insertion device according to claim 1, wherein the first and second jaws each comprise a separator interface that abuts the spacer when the spacer inserts between the first and second jaws and urges the first and second jaws to their engaged positions.

12. The implant insertion device according to claim 11, wherein the spacer pivotably connects with the body and comprises:
an actuator adapted to allow movement of the spacer between its unlocked and locked positions; and
a separator that inserts between the first and second jaws and abuts the separator interfaces of the first and second jaws to urge the first and second jaws to their engaged positions.

13. The implant insertion device according to claim 12, wherein the separator defines a space that allows the separator to insert between the first and second jaws without contacting the shape memory implant.

14. The implant insertion device according to claim 1, wherein the body comprises a handle to allow manipulation of the shape memory implant insertion device and delivery of the shape memory implant into tissue or bone.

15. The implant insertion device according to claim 1, wherein the first arm is shorter in length than the second arm such that the implant insertion device is adapted to receive a shape memory implant with a first bridge at a height different from a second bridge.

16. The implant insertion device according to claim 1, wherein the spacer in its locked position inserts between the first arm and the second arm instead of the first jaw and the second jaw thereby urging the first and second jaws to their engaged positions such that the first and second jaws engage the shape memory implant and move the shape memory implant from its first shape to its second shape, further wherein the first and second jaws in their engaged positions maintain the shape memory implant in the second shape.

17. The implant insertion device according to claim 1, wherein the spacer in its locked position inserts between both the first arm and the second arm and the first jaw and the second jaw thereby urging the first and second jaws to their engaged positions such that the first and second jaws engage the shape memory implant and move the shape memory implant from its first shape to its second shape, further wherein the first and second jaws in their engaged positions maintain the shape memory implant in the second shape.

18. An implant insertion system, comprising:
a shape memory implant movable between a first shape a second shape;
an implant insertion device adapted to receive the shape memory implant in its first shape, manipulate the shape memory implant from its first shape to its second shape, and maintain the shape memory implant in its second shape such that the implant insertion device is adapted for packaging loaded with the shape memory implant in its second shape; and
the implant insertion device, comprising:
a body, comprising:
a first arm including a first jaw adapted to engage the shape memory implant, and
a second arm including a second jaw adapted to engage the shape memory implant, wherein the first jaw and the second jaw are movable from a disengaged position to an engaged position, and
a spacer coupled with the body and movable between an unlocked position and a locked position, wherein the spacer in its locked position inserts between the first jaw and the second jaw and urges the first and second jaws to their engaged positions such that the first and second jaws engage the shape memory implant and move the shape memory implant from its first shape to its second shape, further wherein the first and second jaws in their engaged positions maintain the shape memory implant in the second shape.

19. The implant insertion system according to claim 18, wherein the packaged implant insertion device loaded with the shape memory implant in its second shape is sterilized.

20. The implant insertion system according to claim 18, wherein the implant insertion device is adapted to deliver the shape memory implant into tissue or bone.

21. The implant insertion system according to claim 20, wherein, after the implant insertion device delivers the shape memory implant into tissue or bone, movement of the spacer from its locked position to its unlocked position releases the spacer from between the first jaw and the second jaw, further wherein the first and second jaws move from their engaged positions to their disengaged positions such that the first and second jaws disengage from the shape memory implant, thereby releasing the shape memory implant and allowing the shape memory implant to move from its second shape to its first shape.

22. The implant insertion system according to claim 18, wherein:
the first arm maintains the first jaw canted downward when the spacer resides in its unlocked position; and
the second arm maintains the second jaw canted downward when the spacer resides in its unlocked position.

23. The implant insertion system according to claim 22, wherein insertion of the spacer between the first and second jaws to its locked position moves the first and second jaws horizontally outward and in an upward arc to their engaged positions such that the first and second jaws engage the shape memory implant and move the shape memory implant from its first shape to its second shape, further wherein the first and second jaws in their engaged positions maintain the shape memory implant in the second shape.

24. The implant insertion system according to claim 18, wherein:
the first jaw comprises a leg interface that abuts a first leg of the shape memory implant when the first jaw resides in its engaged position; and
the second jaw comprises a leg interface that abuts a second leg of the shape memory implant when the second jaw resides in its engaged position.

25. The implant insertion system according to claim 24, wherein:
the first jaw comprises a bridge interface, wherein, when the first jaw resides in its engaged position, at least a portion of a bridge of the shape memory implant resides atop the bridge interface; and
the second jaw comprises a bridge interface, wherein, when the second jaw resides in its engaged position, at least a portion of a bridge of the shape memory implant resides atop the bridge interface.

26. The implant insertion system according to claim 25, wherein:
the first jaw comprises a stop disposed above the bridge interface, the stop and the bridge interface defining a slot wherein, when the first jaw resides in its engaged position, at least a portion of a bridge of the shape memory implant resides in the slot; and
the second jaw comprises a stop disposed above the bridge interface, the stop and the bridge interface defining a slot wherein, when the second jaw resides in its engaged position, at least a portion of a bridge of the shape memory implant resides in the slot.

27. The implant insertion system according to claim 18, wherein the first and second jaws each comprise a separator interface that abuts the spacer when the spacer inserts between the first and second jaws and urges the first and second jaws to their engaged positions.

28. The implant insertion system according to claim 27, wherein the spacer pivotably connects with the body and comprises:
an actuator adapted to allow movement of the spacer between its unlocked and locked positions; and
a separator that inserts between the first and second jaws and abuts the separator interfaces of the first and second jaws to urge the first and second jaws to their engaged positions.

29. The implant insertion system according to claim 28, wherein the separator defines a space that allows the separator to insert between the first and second jaws without contacting the shape memory implant.

30. The implant insertion system according to claim 18, wherein the body comprises a handle to allow manipulation of the implant insertion device and delivery of the shape memory implant into tissue or bone.

31. The implant insertion system according to claim 18, wherein:
the shape memory implant comprises a first bridge at a height different from a second bridge; and
the first arm is shorter in length than the second arm such that the implant insertion device receives the first bridge and the second bridge of the shape memory implant.

32. The implant insertion system according to claim 18, wherein the spacer in its locked position inserts between the first arm and the second arm instead of the first jaw and the second jaw thereby urging the first and second jaws to their engaged positions such that the first and second jaws engage the shape memory implant and move the shape memory implant from its first shape to its second shape, further wherein the first and second jaws in their engaged positions maintain the shape memory implant in the second shape.

33. The implant insertion system according to claim 18, wherein the spacer in its locked position inserts between both the first arm and the second arm and the first jaw and the second jaw thereby urging the first and second jaws to their engaged positions such that the first and second jaws engage the shape memory implant and move the shape memory implant from its first shape to its second shape, further wherein the first and second jaws in their engaged positions maintain the shape memory implant in the second shape.

34. A method of securing a first bone, bone fragment, or tissue with a second bone, bone fragment, or tissue, comprising:
i. providing a shape memory implant movable between a first shape a second shape;
ii. contacting first and second jaws of an implant insertion device with the shape memory implant in its first shape;
iii. moving a spacer of the implant insertion device from an unlocked position to a locked position whereby the spacer inserts between the first and second jaws thereby urging the first and second jaws to engage the shape memory implant and move the shape memory implant from its first shape to its second shape, further wherein the first and second jaws maintain the shape memory implant in the second shape;
iv. positioning the first bone, bone fragment, or tissue relative to the second bone, bone fragment, or tissue;
v. positioning the shape memory implant at the first bone, bone fragment, or tissue and the second bone, bone fragment, or tissue using the implant insertion device;
vii. inserting the shape memory implant into the first bone, bone fragment, or tissue and the second bone, bone fragment, or tissue using the implant insertion device;
viii. moving the spacer from between the first jaw and the second jaw thereby releasing the shape memory implant from the first and second jaws; and
ix. removing the implant insertion device from the shape memory implant such that the shape memory implant moves from its second shape to its first shape, thereby securing the first bone, bone fragment, or tissue with the second bone, bone fragment, or tissue.

35. The method according to claim 34, wherein step viii further comprises moving the spacer from between the first jaw and the second jaw at controlled rate of speed, thereby releasing the shape memory implant from the first and second jaws in a controlled fashion.

36. The method of securing a first bone, bone fragment, or tissue with a second bone, bone fragment, or tissue according to claim 34, further comprising:
x. tamping the shape memory implant into the first bone, bone fragment, or tissue and the second bone, bone fragment, or tissue after removing the implant insertion device from the shape memory implant.

37. A method of loading an implant insertion device with a shape memory implant, comprising:
i. providing a shape memory implant movable between a first shape a second shape;
ii. contacting first and second jaws of an implant insertion device with the shape memory implant in its first shape;

iii. reducing the shape memory implant to a temperature at or below a deformation temperature of the shape memory implant; and iv. moving a spacer of the implant insertion device from an unlocked position to a locked position whereby the spacer inserts between the first and second jaws thereby urging the first and second jaws to engage the shape memory implant and move the shape memory implant from its first shape to its second shape, further wherein the first and second jaws maintain the shape memory implant in the second shape.

38. The method of loading an implant insertion device with a shape memory implant according to claim 37, further comprising:

v. packaging the implant insertion device loaded with the shape memory implant in its second shape.

39. The method of loading an implant insertion device with a shape memory implant according to claim 38, further comprising:

vi. sterilizing the packaged implant insertion device loaded with the shape memory implant in its second shape.

40. The method of loading an implant insertion device with a shape memory implant according to claim 37, wherein step iv. comprises:

a. placing the implant insertion device having its first and second jaws contacted with the shape memory implant in its first shape in a press tool;

b. activating the press tool to press the implant insertion device and the shape memory implant such that the spacer of the implant insertion device inserts between the first and second jaws thereby urging the first and second jaws to engage the shape memory implant and move the shape memory implant from its first shape to its second shape, wherein the implant insertion device maintains the shape memory implant in the second shape; and c. removing the implant insertion device loaded with the shape memory implant in its second shape from the press tool.

41. The method of loading an implant insertion device with a shape memory implant according to claim 40, wherein the press tool comprises:

a base that receives thereon the implant insertion device having its first and second jaws contacted with the shape memory implant in its first shape;

a shaft movable to exert a pressing force on the implant insertion device and the shape memory implant; and a bumper coupled with the shaft that engages the implant insertion device and the shape memory implant.

42. A method of loading an implant insertion device with a shape memory implant, comprising:

i. providing a shape memory implant movable between a first shape a second shape;

ii. providing an implant insertion device movable between an implant disengagement position and an implant engagement position, the implant insertion device, comprising first and second jaws adapted to engage the shape memory implant and a spacer movable between an unlocked position and a locked position whereby the spacer inserts between the first and second jaws;

iii. contacting the shape memory implant in its first shape with the implant insertion device in its implant disengagement position;

iv. placing the shape memory implant contacted with the implant insertion device in a press tool;

v. activating the press tool to press the implant insertion device and the shape memory implant such that the spacer moves from its unlocked position to its locked position between the first jaw and the second jaw, thereby moving the implant insertion device from its implant disengagement position to its implant engagement position, wherein the implant insertion device moves the shape memory implant from its first shape to its second shape, further wherein the implant insertion device maintains the shape memory implant in the second shape; and vi. removing the implant insertion device loaded with the shape memory implant in its second shape from the press tool.

43. The method of loading an implant insertion device with a shape memory implant according to claim 42, further comprising:

vii. packaging the implant insertion device loaded with the shape memory implant in its second shape.

44. The method of loading an implant insertion device with a shape memory implant according to claim 43, further comprising:

viii. sterilizing the packaged implant insertion device loaded with the shape memory implant in its second shape.

45. The method of loading an implant insertion device with a shape memory implant according to claim 44, further comprising reducing the shape memory implant to a temperature at or below a deformation temperature of the shape memory implant prior to step iv.

46. The method of loading an implant insertion device with a shape memory implant according to claim 43, wherein the press tool comprises:

a base that receives thereon the implant insertion device having its first and second jaws contacted with the shape memory implant in its first shape;

a shaft movable to exert a pressing force on the implant insertion device and the shape memory implant; and a bumper coupled with the shaft that engages the implant insertion device and the shape memory implant.

47. A method of loading implant insertion devices with shape memory implants, comprising:

i. providing a plurality of shape memory implants movable between a first shape a second shape;

ii. providing a plurality of implant insertion devices movable between an implant disengagement position and an implant engagement position;

iii. contacting each shape memory implant in its first shape with one of the implant insertion devices in its implant disengagement position;

iv. reducing each shape memory implant contacted with one of the implant insertion devices to a temperature at or below a deformation temperature of the shape memory implants;

v. placing a shape memory implant contacted with an implant insertion device in a press tool;

vi. activating the press tool to press the implant insertion device and the shape memory implant to move the implant insertion device from its implant disengagement position to its implant engagement position, wherein the implant insertion device moves the shape memory implant from its first shape to its second shape, further wherein the implant insertion device maintains the shape memory implant in the second shape;

vii. removing the implant insertion device loaded with the shape memory implant in its second shape from the press tool; and viii. repeating steps v.-vii. until each implant insertion device is loaded with one of the shape memory implants in its second shape.

48. The method of loading implant insertion devices with shape memory implants, according to claim 47, further comprising:
ix. packaging the implant insertion devices loaded with the shape memory implants in their second shape.

49. The method of loading implant insertion devices with shape memory implants, according to claim 48, further comprising:
x. sterilizing the packaged implant insertion devices loaded with the shape memory implants in their second shape.

50. The method of loading implant insertion devices with shape memory implants, according to claim 47, wherein:
each implant insertion device comprises first and second jaws adapted to engage the shape memory implant and a spacer adapted for insertion between the first and second jaws; and
activating the press tool to press the implant insertion device and the shape memory implant inserts the spacer between the first and second jaws thereby urging the first and second jaws to engage the shape memory implant and move the shape memory implant from its first shape to its second shape, wherein the implant insertion device maintains the shape memory implant in the second shape.

51. The method of loading implant insertion devices with a shape memory implants according to claim 50, wherein the press tool comprises:
a base that receives thereon the implant insertion device having its first and second jaws contacted with the shape memory implant in its first shape;
a shaft movable to exert a pressing force on the implant insertion device and the shape memory implant; and
a bumper coupled with the shaft that engages the implant insertion device and the shape memory implant.

52. The method of loading implant insertion devices with shape memory implants according to claim 47, wherein step iv. comprises placing each shape memory implant contacted with one of the implant insertion devices in a cryo-freezer.

53. The method of loading implant insertion devices with shape memory implants according to claim 52, wherein step iv. further comprises maintaining each shape memory implant contacted with one of the implant insertion devices at or below the deformation temperature of the shape memory implants after removal from the cryo-freezer.

54. The method of loading implant insertion devices with shape memory implants according to claim 53, wherein maintaining each shape memory implant contacted with one of the implant insertion devices at or below the deformation temperature of the shape memory implants after removal from the cryo-freezer comprises placing each shape memory implant contacted with one of the implant insertion devices on a cold table.

* * * * *